(12) United States Patent
Hauel et al.

(10) Patent No.: US 8,372,838 B2
(45) Date of Patent: Feb. 12, 2013

(54) COMPOUNDS AS BRADYKININ B1 ANTAGONISTS

(75) Inventors: Norbert Hauel, Schemmerhofen (DE); Angelo Ceci, Mittelbiberach (DE); Henri Doods, Warthausen (DE); Ingo Konetzki, Aachen-Oberforstbach (DE); Juergen Mack, Biberach (DE); Henning Priepke, Biberach (DE); Annette Schuler-Metz, Ulm (DE); Rainer Walter, Biberach (DE); Dieter Wiedenmayer, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 39 days.

(21) Appl. No.: 13/031,895

(22) Filed: Feb. 22, 2011

(65) Prior Publication Data

US 2012/0142695 A1    Jun. 7, 2012

(30) Foreign Application Priority Data

Feb. 23, 2010   (WO) ................. PCT/EP2010/052232

(51) Int. Cl.
*A61K 31/50*    (2006.01)
*A61K 31/501*   (2006.01)
(52) U.S. Cl. .................. 514/252.03; 514/248; 544/224; 544/238
(58) Field of Classification Search .................. 544/322; 546/309; 564/121
See application file for complete search history.

(56) References Cited

U.S. PATENT DOCUMENTS 6,689,778 B2 *   2/2004   Bemis et al. ............... 514/235.8
2010/0240669 A1 *  9/2010  Hauel et al. ............... 514/252.05
2011/0263626 A1   10/2011  Hauel et al.

FOREIGN PATENT DOCUMENTS

| WO | 03065789 A2 | 8/2003 |
| WO | WO 03066577 A1 * | 8/2003 |
| WO | WO 2004019868 A2 * | 3/2004 |
| WO | WO 2005016886 A1 * | 2/2005 |
| WO | WO 2005085198 A2 * | 9/2005 |

OTHER PUBLICATIONS

International Search Report for PCT/EP2010/052232, Mailed Aug. 5, 2010.*
International Search Report, Form PCT/ISA/210, for corresponding PCT/EP2011/052512; date of mailing, May 5, 2011.
Kuduk et al.; Development of Orally Bioavailable and CNS Penetrant Biphenylaminocyclopropane Carboxamide Bradykinin B1 Receptor Antagonists; Journal of Medicinal Chemistry/ 2007; vol. 50; pp. 272-282.
Kuduk et al.; Bradykinin B1 antagonists: SAR studies in the 2,3-diaminopyridine series; Bioorganic & Medicinal Chemistry Letters; 2005; No. 15; pp. 3925-3929.
Kuduk et al.; Bradykinin B1 antagonists: Biphenyl SAR studies in the cyclopropanecarboxamide series; Bioorganic & Medicinal Chemistry Letters; 2007; No. 17; pp. 3608-3612.

* cited by examiner

*Primary Examiner* — James O Wilson
*Assistant Examiner* — Alexander R Pagano
(74) *Attorney, Agent, or Firm* — Michael P. Morris; Alan R. Stempel

(57) ABSTRACT

Compounds of the formula I

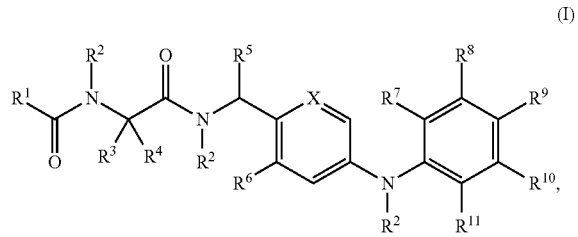

wherein n, $R^1$, $R^2$, $R^3$, $R^4$, $R^5$, $R^6$, $R^7$, $R^8$, $R^9$, $R^{10}$, $R^{11}$ and X are defined as described in the specification, which are bradykinin B1 antagonists, and their use as medicaments.

15 Claims, No Drawings

COMPOUNDS AS BRADYKININ B1 ANTAGONISTS

The present invention relates to the compounds of general formula I

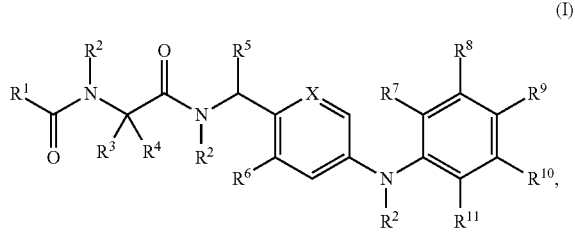

wherein n, $R^1$, $R^2$, $R^3$, $R^4$, $R^5$, $R^6$, $R^7$, $R^8$, $R^9$, $R^{10}$, $R^{11}$ and X are as defined hereinafter, the enantiomers, the diastereomers, the mixtures and the salts thereof, particularly the physiologically acceptable salts thereof with organic or inorganic acids or bases, which have valuable properties, the preparation thereof, the medicaments containing the pharmacologically effective compounds, the preparation thereof and the use thereof.

BACKGROUND TO THE INVENTION

1. Technical Field

The present invention relates to 3-oxo-pyridazine compounds and their use as B1-receptor antagonists, pharmaceutical compositions containing these compounds and methods of using them for the prevention or treatment of acute pain, visceral pain, neuropathic pain, inflammatory pain and pain receptor-mediated pain, tumour pain and headaches.

2. Prior Art

Compounds with a B1-antagonistic activity have already been described in International Patent Application PCT/EP2010/052232 or in the priority application on which it is based.

One aim of the present invention was to provide new compounds which are suitable in particular as pharmaceutical active substances that can be used for the treatment of diseases at least partly mediated by the B1 receptor.

An essential structural feature of the new compounds is the 6-oxo-1,6-dihydro-pyridazine-4-carboxylic acid amide group that is present in tautomeric equilibrium with the 6-hydroxy-pyridazine-4-carboxylic acid amide group:

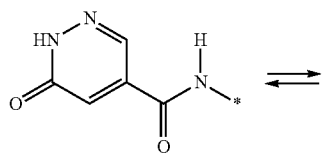

Compared with the compounds from the prior art, the new substances are characterised in that they exhibit a strong B1-receptor blocking activity and at the same time have improved metabolic stability.

DETAILED DESCRIPTION OF THE INVENTION

In the above general formula I in one embodiment 1 $R^1$ denotes the group

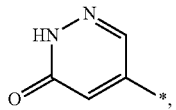

$R^2$ denotes H or $CH_3$,
$R^3$ and $R^4$ together with the carbon atom to which they are bound denote a $C_{3-6}$-cycloalkylene group wherein a —$CH_2$— unit may be replaced by an oxygen atom,
$R^5$ denotes H or $CH_3$,
$R^6$ denotes H, F, Cl or methyl,
$R^7$ denotes H, F, Cl, Br, —CN, $C_{1-4}$-alkyl, $CF_3$, $CHF_2$,
$R^8$ denotes H,
$R^9$ denotes F, Cl, Br, $C_{1-4}$-alkyl, —O—$C_{1-4}$-alkyl, —S—$C_{1-4}$-alkyl,
$R^{10}$ denotes H,
$R^{11}$ denotes F, Cl, Br, —CN, $C_{1-4}$-alkyl, $CF_3$, $CHF_2$, and
X denotes CH or N,
the enantiomers, the diastereomers, the mixtures and the salts thereof, particularly the physiologically acceptable salts thereof with organic or inorganic acids or bases.

An embodiment 2 of the present invention comprises the compounds of general formula I, wherein n, $R^1$, $R^3$, $R^4$, $R^5$, $R^6$, $R^7$, $R^8$, $R^9$, $R^{10}$, $R^{11}$ and X are defined as described hereinbefore in embodiment 1 and
$R^2$ denotes H,
the enantiomers, the diastereomers, the mixtures and the salts thereof, particularly the physiologically acceptable salts thereof with organic or inorganic acids or bases.

The following are mentioned for example as most particularly preferred compounds of the above general formula I:

| No. | Structure |
|---|---|
| (1) | 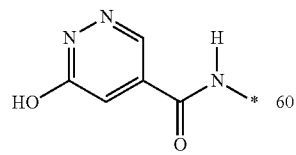 |
| (2) | 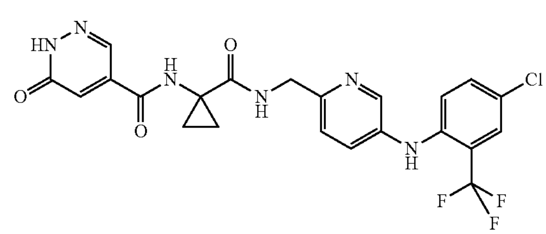 [SMILES: O=C(NC1(C(=O)NCc2ccc(Nc3ccc(Cl)cc3C(F)(F)F)cn2)CC1)c1cn[nH]c(=O)c1] |

-continued

| No. | Structure |
|---|---|
| (3) | (pyridazinone-carboxamide linked to tetrahydrofuran, benzyl, NH-aryl with 4-F and 2-CF₃) |
| (4) | (pyridazinone-carboxamide linked to tetrahydrofuran, benzyl, NH-aryl with 4-Cl and 2-CF₃) |
| (5) | (pyridazinone-carboxamide linked to tetrahydrofuran, benzyl, NH-aryl with 2-CF₃) |
| (6) | (pyridazinone-carboxamide linked to tetrahydrofuran, fluoro-benzyl, NH-aryl with 4-F and 2-CF₃) |
| (7) | (pyridazinone-carboxamide linked to tetrahydrofuran, fluoro-benzyl, NH-aryl with 4-Cl and 2-CF₃) |
| (8) | (pyridazinone-carboxamide linked to tetrahydrofuran, benzyl, NH-aryl with 4-Br and 2-CF₃) |
| (9) | (pyridazinone-carboxamide linked to tetrahydrofuran, fluoro-benzyl, NH-aryl with 2-CF₃) | the enantiomers, the diastereomers, the mixtures and the salts thereof, particularly the physiologically acceptable salts thereof with organic or inorganic acids or bases.

TERMS AND DEFINITIONS USED

Unless otherwise stated, all the substituents are independent of one another. If for example there are a plurality of $C_{1-4}$-alkyl groups as substituents in one group, in the case of three substituents $C_{1-4}$-alkyl, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

Also included in the subject matter of this invention are the compounds according to the invention, including the salts thereof, in which one or more hydrogen atoms, for example one, two, three, four or five hydrogen atoms, are replaced by deuterium.

By the term "$C_{1-4}$-alkyl" (including those that are part of other groups) are meant alkyl groups with 1 to 4 carbon atoms. Examples include: methyl, ethyl, n-propyl, iso-propyl, n-butyl, iso-butyl, sec-butyl and tert-butyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl.

Moreover the definitions mentioned previously also include those groups wherein each methylene group may be substituted by up to two and each methyl group may be substituted by up to three fluorine atoms.

By the term "$C_{3-6}$-cycloalkyl" (including those that are part of other groups) are meant cyclic alkyl groups with 3 to 6 carbon atoms. Examples include: cyclopropyl, cyclobutyl, cyclopentyl or cyclohexyl.

If they contain suitable basic functions, for example amino groups, compounds of general formula I may be converted, particularly for pharmaceutical use, into the physiologically acceptable salts thereof with inorganic or organic acids. Examples of inorganic acids for this purpose include hydrobromic acid, phosphoric acid, nitric acid, hydrochloric acid, sulphuric acid, methanesulphonic acid, ethanesulphonic acid, benzenesulphonic acid or p-toluenesulphonic acid, while organic acids that may be used include malic acid, succinic acid, acetic acid, fumaric acid, maleic acid, mandelic acid, lactic acid, tartaric acid or citric acid.

In addition, the compounds of general formula I, if they contain suitable carboxylic acid functions, may be converted into the physiologically acceptable salts thereof with inorganic or organic bases, particularly for pharmaceutical applications. Examples of inorganic bases include alkali or alkaline earth metal hydroxides, e.g. sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The compounds according to the invention may be present as racemates, provided that they have only one chiral element, but may also be obtained as pure enantiomers, i.e. In the (R) or (S) form.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

Compounds with a carbon double bond may be present in both the E and Z form.

If a compound is present in different tautomeric forms, the compound prepared is not limited to one tautomeric form but includes all the tautomeric forms. This also applies particularly to nitrogen-containing heteroaryls:

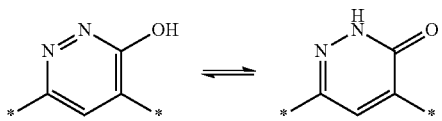 [SMILES: *c1cc(*)c(O)nn1 ; *c1cc(*)c(=O)[nH]n1]

Preparation Methods

According to the invention the compounds of general formula I are obtained by methods known per se, for example by the following methods:
(A) amide coupling:

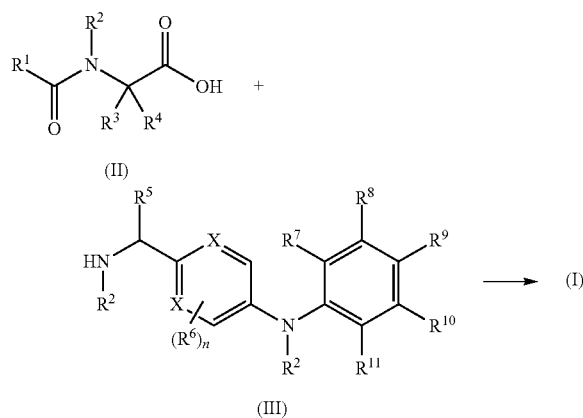

The linking of carboxylic acids of general formula II as shown, wherein all the groups are as hereinbefore defined, with amines of general formula III, wherein all the groups are as hereinbefore defined, to form carboxylic acid amides of general formula I wherein all the groups are as hereinbefore defined, may be carried out by conventional methods of amide formation.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran (THF), acetonitrile, dimethyl formamide (DMF), dimethyl acetamide (DMA), N-methylpyrrolidone (NMP) or mixtures. If necessary, an auxiliary base such as diisopropylethylamine (DIPEA, Hübase) is additionally used.
B) Amide coupling:

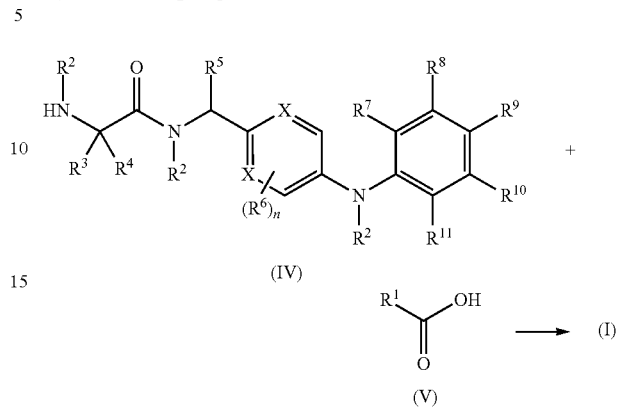

An alternative method of preparing compounds of general formula I consists in linking carboxylic acids of general formula V, wherein all the groups are as hereinbefore defined, with amines of general formula IV, wherein all the groups are as hereinbefore defined.

The compounds of general formula V are either commercially obtainable or may be prepared by methods known from the literature It is also possible to convert the carboxylic acids of general formula V into carboxylic acid chlorides and then react these with amines of general formula IV. Carboxylic acid chlorides are synthesised by methods known from the literature (cf. e.g. Houben-Weyl, Methoden der Organischen Chemie, vol. E5/1).
(C) Reduction of the nitrile group:

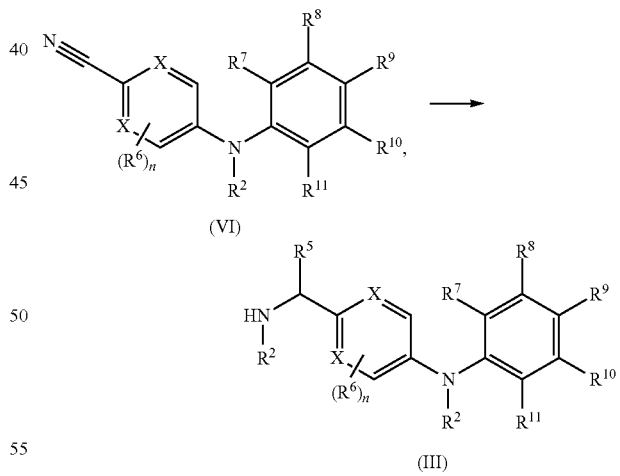

The reduction of a nitrile of general formula VI to an amine of general formula III, wherein the group $R^2$ at the amine nitrogen denotes hydrogen and all the other groups are as hereinbefore defined, may be carried out under standard conditions of catalytic hydrogenolysis with a catalyst such as Raney nickel, for example, in a solvent such as ammoniacal methanol or ethanol or with a reducing agent such as lithium aluminium hydride or sodium borohydride in a solvent such as tetrahydrofuran, optionally in the presence of a Lewis acid such as aluminium chloride.

Compounds of general formula III, wherein the group $R^2$ at the amine nitrogen denotes not hydrogen but an alkyl group, for example, may also be prepared from compounds of general formula VI. Thus, for example, the reaction of a nitrile of general formula VI with an alkyl Grignard reagent produces ketones which can be converted by reductive amination into the compounds of general formula III. The reductive amination is carried out using known methods, for example with a reducing agent such as sodium triacetoxyborohydride, sodium borohydride or sodium cyanoborohydride, conveniently in a solvent such as tetrahydrofuran or dichloromethane optionally substituted by the addition of acetic acid.

Alternatively the ketones obtained may also be converted into oximes. The subsequent reduction of the oximes then yields compounds of general formula III.

(D) nucleophilic aromatic substitution or transition-metal-catalysed coupling:

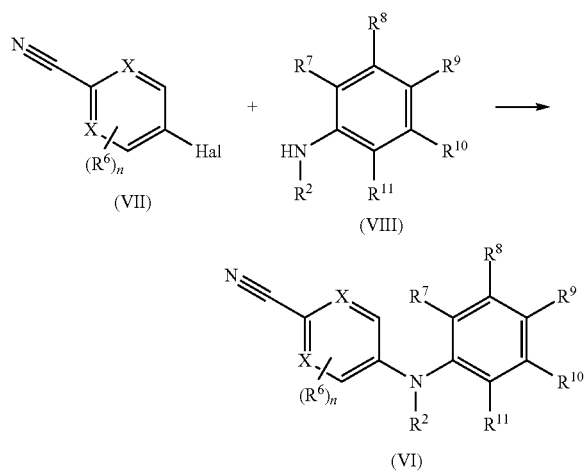

The reaction of an aniline of general formula VIII, wherein all the groups are as hereinbefore defined, with a nitrile of general formula VII, wherein X, $R_6$ and n are as hereinbefore defined, and Hal denotes a fluorine, chlorine or bromine atom, is carried out using known methods, for example in a solvent such as tetrahydrofuran, dimethylformamide or dimethylsulphoxide and conveniently in the presence of a base such as triethylamine, sodium hydroxide solution or potassium carbonate at a temperature of 20° C. to 160° C. If the aniline of general formula VIII is liquid, the reaction may also be carried out without a solvent and additional base.

An alternative method of preparing compounds of general formula VI is the palladium-catalysed reaction of a nitrile of general formula VII, wherein Hal denotes bromine or chlorine, with an aniline of general formula VIII. Reaction conditions for this reaction, which is also known as a Buchwald-Hartwig reaction, are known from the literature.

Description of the Method of Binding the CynoBK1-Receptor

CHO cells that express the cynomolgus BK1-receptor are cultivated in "HAM'S F-12 Medium". The medium is removed from confluent cultures, the cells are washed with PBS buffer, scraped off or detached using Versene and isolated by centrifuging. Then the cells are homogenised in suspension, the homogenate is centrifuged and resuspended. After the protein content has been determined 200 µl of the homogenate (50 to 250 µg protein/assay) are incubated for 60-180 minutes at ambient temperature with 0.5 to 5.0 nM kallidine (DesArg10,Leu9), [3,4-Prolyl-3,43H(N)] and increasing concentrations of the test substance in a total volume of 250 µl. The incubation is stopped by rapid filtration through GF/B glass fibre filters that have been pre-treated with polyethyleneimine (0.3%). The radioactivity bound to the protein is measured with a TopCount NXT. The radioactivity bound in the presence of 1.0 µM kallidine (DesArg10) is defined as non-specific binding. The concentration binding curve may be analysed using computer-aided non-linear curve fitting to determine the corresponding $K_i$ value for the test substance.

Test results of the cynoBK1-receptor binding assay:

| Example No. | $K_i$ [nM] |
| --- | --- |
| (1) | 3.5 |
| (2) | 5.1 |
| (3) | 12 |
| (4) | 27 |
| (5) | 11 |
| (6) | 3.2 |
| (7) | 30 |
| (8) | 37 |
| (9) | 6.6 |

An essential structural feature of the new compounds is the 6-oxo-1,6-dihydro-pyridazine-4-carboxylic acid amide group which is contained in all the compounds according to the invention and is in tautomeric equilibrium with the 6-hydroxy-pyridazine-4-carboxylic acid amide group:

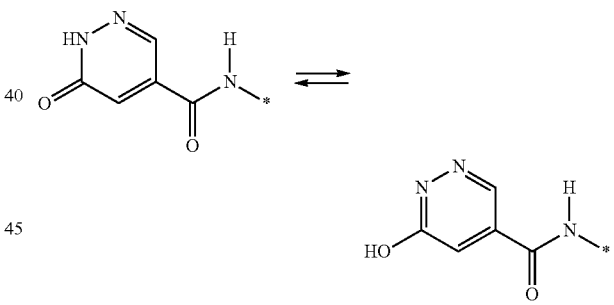

Compared with the compounds from the prior art the new substances are characterised in that they exhibit a very strong B1-receptor blocking activity and at the same time have much better metabolic stability. The metabolic stability can be measured by determining the decomposition in human hepatocytes and using the rate of decomposition to calculate the clearance, which in turn is expressed as a percentage of the human hepatic blood flow (% Qh). A substance with a high metabolic clearance (e.g. >70% Qh) will presumably exhibit a shorter duration of activity in the human body than a substance that is metabolically more stable and thus has a lower clearance (e.g. <30% Qh). Thus, in the interests of achieving a long duration of activity it is highly advantageous if the active substance has a high metabolic stability (low clearance). Surprisingly the new substances exhibit a low clearance in human hepatocytes, as is apparent from the following Table:

| Example No. | $K_i$ [nM] | Clearance [% Qh] |
|---|---|---|
| (1) | 3.5 | 1 |
| (3) | 12 | 7 |
| (5) | 11 | 22 |
| (6) | 3.2 | 6 |

Description of Method for Determining Metabolic Clearance in Human Hepatocytes

The metabolic breakdown of the test substance is determined in a hepatocyte suspension. Cryopreserved primary human hepatocytes are incubated in a suitable incubation medium (e.g. Dulbecco's modified eagle medium, DMEM) which contains 5% human serum. After 30 minutes' pre-incubation in the incubator (37° C., 10% carbon dioxide) 5 µL of the test compound (80 µM, prepared from a 2 mM stock solution in dimethylsulphoxide and diluted 1:25 with incubation medium) are added to 395 µL of hepatocyte suspension (cell density in the range from 0.25-1 million cells/mL, typically 1 million cells/mL; final concentration of the test compound 1 µM). The cells are incubated for 6 hours in an incubator with an orbital agitator. At times 0, 0.5, 1, 2, 4 and 6 h, 25 µL of the medium are removed in each case. The medium removed is mixed with an excess of acetonitrile and centrifuged for 5 minutes. The supernatant is removed, evaporated to dryness under nitrogen and taken up in a mixture of 25% methanol and 0.1% formic acid. The reduction in the concentration of the test substance in the incubation medium is determined by coupling liquid chromatography with electrospray mass spectrometry. The linear phase of the decrease in the concentration of the test substance in the medium is used for the calculation. The intrinsic clearance is calculated as follows: CL_INTRINSIC=dose/AUC=(C0/CD)/(AUD+clast/k)×1000/60. C0: initial concentration in the incubation [µM], CD: cell density of the vital cells [10e6cells/mL], AUD: area under the curve [µM×h], clast: concentration of the last data point [µM], k: increase in the regression lines for the reduction in the test substance [h−1]. The intrinsic in vitro clearance calculated is now converted into the intrinsic in vivo clearance:

CL_INTRINSIC_INVIVO [ml/min/kg]=
    (CL_INTRINSIC [µL/min/10e6cells]×
    hepatocellularity [10e6 cells/g liver]×
    liver factor [g/kg body weight])/1000 and the estimated human clearance is calculated using the well-stirred model:

CL [ml/min/kg]=CL_INTRINSIC_INVIVO [ml/min/kg]×
    hepatic blood flow [ml/min/kg]/(CL_INTRIN-
    SIC_INVIVO [ml/min/kg]+hepatic blood flow
    [ml/min/kg]).

The following parameters are used for the calculation: hepatocellularity, human: 120×10e6 cells/g liver; liver factor, human: 25.7 g liver/kg body weight; hepatic blood flow, human: 21 ml/(min×kg).

Indications

In view of their pharmacological properties, the novel compounds and their physiologically acceptable salts are suitable for treating diseases and symptoms of diseases caused at least to some extent by stimulation of bradykinin-B1 receptors, or in which antagonisation of the of bradykinin-B1 receptor can bring about an improvement in symptoms.

In a further aspect the present invention encompasses the compounds of the above-mentioned general formula I according to the invention for use as medicaments.

In view of their pharmacological effect the substances are suitable for the treatment of (a) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus;

(b) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(c) neuropathic pain such as for example painful neuropathies, pain of diabetic neuropathy, AIDS-associated neuropathic pain non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves, and central pain such as for example pain after stroke, spinal injuries or tumours;

d) inflammatory/pain receptor-mediated pain in connection with diseases such as for example osteoarthritis, rheumatoid arthritis, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns, (e) tumour pain associated with cancers such asfe lymphatic or myeloid leukaemia, Hodgkin's disease, non-Hodgkin's lymphomas, lymphogranulomatosis, lymphosarcomas, solid malignant tumours and extensive metastases;

(f) headache diseases of various origins, such as for example cluster headaches, migraine (with or without aura) and tension headaches.

(g) painful conditions of mixed origin, such as for example chronic back pain including lumbago, or fibromyalgia.

The compounds are also suitable for treating (h) inflammatory complaints or phenomena caused by sunburn and burns, inflammation of the gums, oedema after burns trauma, cerebral oedema and angiooedema, intestinal complaints including Crohn's disease and ulcerative colitis, irritable bowel syndrome, pancreatitis, nephritis, cystitis (interstitial cystitis), uveitis; inflammatory skin diseases (such as psoriasis and eczema), vascular diseases of the connective tissue, sprains and fracture, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome;

(i) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;

(j) chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, cystic fibrosis, bronchiectasis, pulmonary diseases in alpha1-antitrypsin deficiency and cough;

(k) diabetes mellitus and its effects (such as e.g. diabetic vasculopathy, diabetic neuropathy, diabetic retinopathy) and diabetic symptoms in insulitis (for example hyperglycaemia, diuresis, proteinuria and increased renal excretion of nitrite and kallikrein);

(l) sepsis and septic shock after bacterial infections or after trauma;

(m) syndromes that cause itching and allergic skin reactions;

(n) damage to the central nervous system;

(O) wounds and tissue damage;

(p) benign prostatic hyperplasia and hyperactive bladder;

(q) vascular diseases such as panarteriitis nodosa, polyarthritis nodosa, periarteriitis nodosa, arteriitis temporalis, Wegner's granulomatosis, giant cell arteriitis, arteriosclerosis and erythema nodosum; inflammation of the gums;

(r) disorders of the motility or spasms of respiratory, genitourinary, gastro-intestinal including biliary or vascular structures and organs;

(s) post-operative fever;

(t) for the treatment and prevention of cardiovascular diseases such as high blood pressure and related complaints;

(u) for the treatment and prevention of cancer and related complaints;

(v) for the treatment and prevention of psychiatric diseases such as depression;

(w) for the treatment and prevention of urinary incontinence and related complaints;

(x) for the treatment and prevention of morbid obesity and related complaints;

(y) for the treatment and prevention of atherosclerosis and related complaints.

(z) for the treatment and prevention of epilepsy.

The substances are suitable for causal treatment in the sense of slowing down or stopping the progress of chronically progressive diseases, particularly osteoarthritis, rheumatoid arthritis and spondylarthritis.

In another aspect the present invention encompasses the use of the compounds of the above-mentioned general formula I according to the invention for preparing a medicament for therapeutic use in the above-mentioned indications.

Preferably, the compounds of general formula I according to the invention are used for the treatment of osteoarthritis, rheumatoid arthritis or COPD.

The term "treatment" or "therapy" refers to a therapeutic treatment of patients with a manifest, acute or chronic indication, including on the one hand symptomatic (palliative) treatment to relieve the symptoms of the disease and on the other hand causal or curative treatment of the indication with the aim of ending the pathological condition, reducing the severity of the pathological condition or delaying the progression of the pathological condition, depending on the nature or gravity of the indication.

The present invention further relates to the use of a compound of general formula I for preparing a medicament for the acute and prophylactic treatment of acute pain, visceral pain, neuropathic pain, inflammatory/pain receptor-mediated pain, tumour pain, headache pain and pain of mixed causes and other diseases as mentioned above. This use is characterised in that it comprises administering an effective amount of a compound of general formula I or a physiologically acceptable salt thereof to a patient requiring such treatment.

The term "patient" preferably refers to a human being.

In addition to their suitability as therapeutic drugs for humans, these substances are also useful in the veterinary medical treatment of domestic pets, exotic animals and farmed animals.

Combinations

For treating pain, it may be advantageous to combine the compounds according to the invention with stimulating substances such as caffeine or other pain-alleviating active compounds. If active compounds suitable for treating the cause of the pain are available, these can be combined with the compounds according to the invention.

The following compounds may be used for combination therapy, for example:

Non-steroidal antirheumatics (NSAR) such as for example propionic acid derivatives which may be selected from among alminoprofen bucloxic acid, carprofen, fenoprofen, ibuprofen, ketoprofen, naproxen, oxaprozin, pirprofen, pranoprofen and tiaprofenic acid; acetic acid derivatives which may be selected from among indomethacin, acemetacin, alclofenac, isoxepac, sulindac and tolmetin; fenamic derivatives which may be selected from among meclofenamic acid, mefenamic acid and tolfenamic acid; biphenyl-carboxylic acid derivatives; oxicams which may be selected from among meloxicam, piroxicam and tenoxicam; salicylic acid derivatives which may be selected from among acetylsalicylic and sulphasalazine; pyrazolones which may be selected from among apazone and feprazone; and coxibs which may be selected from among celecoxib and etoricoxib). Opiate receptor agonists which may for example be selected from among morphine, Darvon, tramadol and buprenorphine;

Cannabinoid agonists such as for example GW-1000;

Sodium channel blockers which may for example be selected from among carbamazepine, mexiletin, pregabalin, tectin and ralfinamide.

N-type calcium channel blockers such as for example ziconotide.

Serotonergic and noradrenergic modulators which may be selected from among for example duloxetine and amitriptyline.

Corticosteroids which may be selected from among for example betamethasone, budesonide, cortisone, dexamethasone, hydrocortisone, methylprednisolone, prednisolone, prednisone and triamcinolone.

Histamine H1-receptor antagonists which may for example be selected from among bromopheniramine, chloropheniramine, dexchloropheniramine, triprolidine, clemastine, diphenhydramine, diphenylpyraline, tripelennamine, hydroxyzine, methdilazine, promethazine, trimeprazine azatadine, cyproheptadine, antazoline, pheniramine, pyrilamine, loratadine, cetirizine, desloratadine, fexofenadine and levocetirizine.

Leukotriene antagonists and 5-lipoxygenase inhibitors which may for example be selected from among zafirlukast, montelukast, pranlukast and zileuton.

Local anaesthetics which may for example be selected from among ambroxol and lidocaine.

TRVP1 antagonists which may for example be selected from among AZD-1386, JTS-653 and PHE-377.

Nicotine receptor agonists such as for example A-366833.

P2×3-receptor antagonists such as e.g. A-317491.

anti-NGF antibodies and NGF antagonists which may for example be selected from among JNJ-42160443 and PPH 207.

NK1 and NK2 antagonists such as e.g. CP-728663.

NMDA antagonists which may for example be selected from among CNS-5161, AZ-756 and V-3381.

Potassium channel modulators such as e.g. CL-888.

GABA modulators such as e.g. baclofen.

Anti-migraine drugs such as e.g. sumatriptan, zolmitriptan, naratriptan and eletriptan.

For treating one or more of the above-mentioned respiratory complaints it may be advantageous to combine the compounds of general formula I according to the invention with other active substances for treating respiratory complaints. If suitable active substances for treating the cause of the respiratory complaints are available, these may be combined with the compounds according to the invention.

The compounds of general formula I may optionally also be used in conjunction with other pharmacologically active substances. It is preferable to use active substances of the type selected from among the betamimetics, anticholinergics, corticosteroids, other PDE4-inhibitors, LTD4-receptor (CysLT1, CysLT2, CysLT3) antagonists, inhibitors of MAP kinases such as for example p38, ERK1, ERK2, JNK1, JNK2, JNK3 or SAP, LTB4-receptor (BLT1, BLT2) antagonists, EGFR-inhibitors, H1-receptor antagonists, antihistamines, H4-receptor antagonists, PAF-antagonists and PI3-kinase inhibitors CXCR1 and/or CXCR2 receptor antagonists and anti-tussives.

The compounds of general formula I may also be used in the form of double or triple combinations thereof, such as for example combinations of compounds of formula I with one or two compounds selected from among betamimetics, corticosteroids, PDE4-inhibitors, EGFR-inhibitors and LTD4-antagonists, anticholinergics, betamimetics, corticosteroids, PDE4-inhibitors, EGFR-inhibitors and LTD4-antagonists, PDE4-inhibitors, corticosteroids, EGFR-inhibitors and LTD4-antagonists, EGFR-inhibitors, PDE4-inhibitors and LTD4-antagonists, EGFR-inhibitors and LTD4-antagonists, CCR3-inhibitors, iNOS-inhibitors (inducible nitric oxide synthase-inhibitors), (6R)-L-erythro-5,6,7,8-tetrahydrobiopterin (hereinafter referred to as "BH4") and the derivatives thereof which are mentioned in WO 2006/120176, and SYK-inhibitors (spleen tyrosine kinase inhibitors), anticholinergics, betamimetics, corticosteroids, PDE4-inhibitors and MRP4-inhibitors.

Combinations of three active substances of one of the above mentioned categories of compounds are also covered by the invention.

Betamimetics used according to the invention are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramid, tolubuterol and zinterol or 6-hydroxy-8-{1-hydroxy-2-[2-(4-methoxy-phenyl)-1,1-dimethyl-ethylamino]-ethyl}-4H-benzo[1,4]oxazin-3-one, 8-{2-[2-(2,4-difluoro-phenyl)-1,1-dimethyl-ethylamino]-1-hydroxy-ethyl}-6-hydroxy-4H-benzo[1,4]oxazin-3-one, 8-{2-[2-(3,5-difluoro-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 8-{2-[2-(4-fluoro-phenyl)-1,1-dimethyl-ethylamino]-1-hydroxy-ethyl}-6-hydroxy-4H-benzo[1,4]oxazin-3-one, N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide, 8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one, N-[2-hydroxy-5-((1R)-1-hydroxy-2-{2-[4-(2-hydroxy-2-phenyl-ethylamino)-phenyl]-ethylamino}-ethyl)-phenyl]formamide, 8-hydroxy-5-((1R)-1-hydroxy-2-{2-[4-(6-methoxy-biphenyl-3-ylamino)-phenyl]-ethylamino}-ethyl)-1H-quinolin-2-one, 8-hydroxy-5-[(1R)-1-hydroxy-2-(6-phenethylamino-hexylamino)-ethyl]-1H-quinolin-2-one, 5-[(1R)-2-(2-{4-[4-(2-amino-2-methyl-propoxy)-phenylamino]-phenyl}-ethylamino)-1-hydroxy-ethyl]-8-hydroxy-1H-quinolin-2-one,

[3-(4-{6-[(2R)-2-hydroxy-2-(4-hydroxy-3-hydroxymethyl-phenyl)-ethylamino]-hexyloxy}-butyl)-5-methyl-phenyl]-urea, 4-((1R)-2-{6-[2-(2,6-dichloro-benzyloxy)-ethoxy]hexylamino}-1-hydroxy-ethyl)-2-hydroxymethyl-phenol, 3-(4-{6-[(2R)-2-hydroxy-2-(4-hydroxy-3-hydroxymethyl-phenyl)-ethylamino]-hexyloxy}-butyl)-benzenesulphonamide, 3-(3-{7-[(2R)-2-hydroxy-2-(4-hydroxy-3-hydroxymethyl-phenyl)-ethylamino]-heptyloxy}-propyl)-benzenesulphonamide, 4-((1R)-2-{6-[4-(3-cyclopentanesulphonyl-phenyl)-butoxy]-hexylamino}-1-hydroxy-ethyl)-2-hydroxymethyl-phenol, N-1-Adamantanyl-2-{3-[(2R)-2-({(2R)-2-hydroxy-2-[4-hydroxy-3-(hydroxymethyl)-phenyl]ethyl}amino)propyl]phenyl}acetamide, (1R)-5-{2-[6-(2.2-difluoro-2-phenyl-ethoxy)-hexylamino]-1-hydroxy-ethyl}-8-hydroxy-1H-quinolin-2-one
(R,S)-4-(2-{[6-(2.2-difluoro-4-phenylbutoxy)hexyl]amino}-1-hydroxy-ethyl)-2-(hydroxyl-methyl)phenol,
(R,S)-4-(2-{[6-(2.2-difluoro-2-phenylethoxy)hexyl]amino}-1-hydroxy-ethyl)-2-(hydroxyl-methyl)phenol,
(R,S)-4-(2-{[4,4-difluoro-6-(4-phenylbutoxy)hexyl]amino}-1-hydroxy-ethyl)-2-(hydroxyl-methyl)phenol,
(R,S)-4-(2-{[6-(4,4-difluoro-4-phenylbutoxy)hexyl]amino}-1-hydroxy-ethyl)-2-(hydroxyl-methyl)phenol,
(R,S)-5-(2-{[6-(2.2-difluoro-2-phenylethoxy)hexyl]amino}-1-hydroxy-ethyl)-8-hydroxyquinolin-2(1H)-one,
(R,S)-[2-({6-(2.2-difluoro-2-(3-methylphenyl)ethoxy]hexyl}amino)-1-hydroxyethyl]-2-(hydroxymethyl)phenol,
4-(1R)-2-{[6-(2.2-difluoro-2-phenylethoxy)hexyl]amino}-1-hydroxyethyl)-2-(hydroxyl-methyl)phenol,
(R,S)-2-(hydroxymethyl)-4-(1-hydroxy-2-{[4.4.515-tetrafluoro-6-(3-phenylpropoxy)-hexyl]amino}ethyl)phenol,
(R,S)-[5-(2-{[6-(2.2-difluoro-2-phenylethoxy)hexyl]amino}-1-hydroxy-ethyl)-2-hydroxy-phenyl]formamide,
(R,S)-4-[2-({6-[2-(3-bromophenyl)-2.2-difluoroethoxy]hexyl}amino)-1-hydroxyethyl]-2-(hydroxymethyl)phenol,
(R,S)—N-[3-(1.1-difluoro-2-{[6-({2-hydroxy-2-[4-hydroxy-3-(hydroxymethyl)phenyl]-ethyl}amino)hexyl]oxy}ethyl)phenyl]-urea,
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidin-2,4-dione,
(R,S)-4-[2-({6-[2.2-difluoro-2-(3-methoxyphenyl)ethoxy]hexyl}amino)-1-hydroxyethyl]-2-(hydroxymethyl)phenol,
5-((1R)-2-{[6-(2.2-difluoro-2-phenylethoxy)hexyl]amino}-1-hydroxyethyl)-8-hydroxyquinolin-2(1H)-one,
4-((1R)-2-{[4,4-difluoro-6-(4-phenylbutoxy)hexyl]amino}-1-hydroxy-ethyl)-2-(hydroxyl-methyl)phenol,
(R,S)-4-(2-{[6-(3.3-difluoro-3-phenylpropoxy)hexyl]amino}-1-hydroxy-ethyl)-2-(hydroxylmethyl)phenol,
(R,S)-(2-{[6-(2.2-difluoro-2-phenylethoxy)-4,4-difluorohexyl]amino}-1-hydroxyethyl)-2-(hydroxymethyl)phenol,
(R,S)-4-(2-{[6-(2.2-difluoro-3-phenylpropoxy)hexyl]amino}-1-hydroxyethyl)-2-(hydroxyl-methyl)phenol,
3-[2-(3-chloro-phenyl)-ethoxy]-N-(2-diethylamino-ethyl)-N-{2-[2-(4-hydroxy-2-oxo-2,3-dihydro-benzothiazole-7-yl)-ethylamino]-ethyl}-propionamide,
N-(2-diethylamino-ethyl)-N-{2-[2-(4-hydroxy-2-oxo-2,3-dihydro-benzothiazole-7-yl)-ethylamino]-ethyl}-3-(2-naphthalen-1-yl-ethoxy)-propionamide,
7-[2-(2-{3-[2-(2-chloro-phenyl)-ethylamino]propylsulphanyl}-ethylamino)-1-hydroxy-ethyl]-4-hydroxy-3H-benzothiazol-2-one, optionally in the form of their racemates, enantiomers, diastereomers and optionally in the form of the pharmacologically acceptable acid addition salts, solvates or hydrates thereof. Preferably, according to the invention, the acid addition salts of the betamimetics are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Anticholinergics used according to the invention are preferably compounds selected from among the tiotropium salts, preferably the bromide salt, oxitropium salts, preferably the bromide salt, flutropium salts, preferably the bromide salt, Ipratropiumsalzen, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthene-9-carbonyloxy)-1-azoniabicyclo[2,2,2]octane salts. In the above-mentioned salts the cations are the pharmacologically active constituents. As anions X⁻ the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while the chloride, bromide, iodide, sulphate, methanesulphonate or p-toluenesulphonate are preferred as counter-ions. Of all the salts the chlorides, bromides, iodides and methanesulphonates are particularly preferred.

Other anticholinergics may be selected from among
tropenol 2,2-diphenylpropionate-methobromide,
scopine 2,2-diphenylpropionate-methobromide,
scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide,
tropenol 9-hydroxy-fluorene-9-carboxylate methobromide,
tropenol 9-fluoro-fluorene-9-carboxylate methobromide,
scopine 9-hydroxy-fluorene-9-carboxylate methobromide,
scopine 9-fluoro-fluorene-9-carboxylate methobromide,
tropenol 9-methyl-fluorene-9-carboxylate methobromide,
scopine 9-methyl-fluorene-9-carboxylate methobromide,
cyclopropyltropine benzilate methobromide,
cyclopropyltropine 2,2-diphenylpropionate methobromide,
cyclopropyltropine 9-hydroxy-xanthene-9-carboxylate methobromide,
cyclopropyltropine 9-methyl-fluorene-9-carboxylate methobromide,
cyclopropyltropin 9-methyl-xanthene-9-carboxylate methobromide,
cyclopropyltropine 9-hydroxy-fluorene-9-carboxylate methobromide,
cyclopropyltropine methyl 4,4'-difluorobenzilate methobromide,
tropenol 9-hydroxy-xanthene-9-carboxylate methobromide,
scopine 9-hydroxy-xanthene-9-carboxylate methobromide,
tropenol 9-methyl-xanthene-9-carboxylate methobromide,
scopine 9-methyl-xanthene-9-carboxylate methobromide,
tropenol 9-ethyl-xanthene-9-carboxylate methobromide,
tropenol 9-difluoromethyl-xanthene-9-carboxylate methobromide, and
scopine 9-hydroxymethyl-xanthene-9-carboxylate methobromide.

The above-mentioned compounds may also be used as salts within the scope of the present invention, wherein the metho-X salts are used instead of the methobromide, where X may have the meanings given for X⁻ hereinbefore.

Corticosteroids used according to the invention are preferably compounds selected from among beclomethasone betamethasone, budesonide, butixocort, ciclesonide, deflazacort, dexamethasone, etiprednol, flunisolide, fluticasone, loteprednol, mometasone, prednisolone, prednisone, rofleponide, triamcinolone and tipredane orpregna-1,4-dien-3,20-dione, 6-fluoro-11-hydroxy-16.17-[(1-methylethyliden)-bis(oxy)]-21-[[4-[(nitroxy)methyl]benzoyl]oxy], (6-alpha,11-beta,16-alpha)-(9Cl) (NCX-1024)

- 16,17-butylidenedioxy-6,9-difluoro-11-hydroxy-17-(methylthio)androst-4-en-3-one (RPR-106541),
- (S)-fluoromethyl 6,9-difluoro-17-[(2-furanylcarbonyl)oxy]-11-hydroxy-16-methyl-3-oxo-androsta-1,4-diene-17-carbothionate,
- (S)-(2-oxo-tetrahydrofuran-3S-yl) 6,9-difluoro-11-hydroxy-16-methyl-3-oxo-17-propionyloxy-androsta-1, 4-diene-17-carbothionate, and
- cyanomethyl 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylate, optionally in the form of their racemates, enantiomers or diastereomers and optionally in the form of the salts and derivatives thereof, the solvates and/or hydrates thereof. Every reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors used according to the invention are preferably compounds selected from among enprofyllin, theophyllin, roflumilast, ariflo (cilomilast), tofimilast, pumafentrin, lirimilast, apremilast, arofyllin, atizoram, oglemilast and tetomilast or

- 5-[(N-(2,5-dichloro-3-pyridinyl)-carboxamid]-8-methoxy-quinoline (D-4418),
- N-(3,5-dichloro-1-oxido-4-pyridinyl)-carboxamid]-8-methoxy-2-(trifluoromethyl)-quinoline (D-4396 (Sch-351591)),N-3,5-dichloropyrid-4-yl)-[1-(4-fluorobenzyl)-5-hydroxy-indol-3-yl]glyoxylamide (AWD-12-281 (GW-842470)), 9-[(2-fluorophenyl)methyl]-N-methyl-2-(trifluoromethyl)-9H-purin-6-amine (NCS-613),
- 4-[(2R)-2-[3-(cyclopentyloxy)-4-methoxyphenyl]-2-phenylethyl]-pyridine (CDP-840),
- N-[(3R)-3,4,6,7-tetrahydro-9-methyl-4-oxo-1-phenylpyrrolo[3,2,1-jk][1,4]benzodiazepin-3-yl]-4-pyridinecarboxamide (PD-168787),
- 4-[6,7-d]ethoxy-2,3-bis(hydroxymethyl)-1-naphthalenyl]-1-(2-methoxyethyl)-2(1H)-pyridinone (T-440),
- 2-[4-[6,7-diethoxy-2,3-bis(hydroxymethyl)-1-naphthalenyl]-2-pyridinyl]-4-(3-pyridinyl)-1(2H)-phthalazinone (T-2585),
- (3-(3-cyclopenyloxy-4-methoxybenzyl)-6-ethylamino-8-isopropyl-3H-purine (V-11294A),
- beta-[3-(cyclopentyloxy)-4-methoxyphenyl]-1,3-dihydro-1,3-dioxo-2H-isoindole-2-propanamide (CDC-801),
- imidazo[1,5-a]pyrido[3,2-e]pyrazin-6(5H)-one, 9-ethyl-2-methoxy-7-methyl-5-propyl-(D-22888)
- 5-[3-(cyclopentyloxy)-4-methoxyphenyl]-3-[(3-methylphenyl)methyl], (3S,5S)-2-piperi-dinone (HT-0712),
- 4-[1-[3,4-bis(difluoromethoxy)phenyl]-2-(3-methyl-1-oxido-4-pyridinyl)ethyl]alpha,alpha-bis(trifluoromethyl)-benzenemethanol (L-826141),
- N-(3,5-dichloro-1-oxo-pyridin-4-yl)-4-difluoromethoxy-3-cyclopropylmethoxybenzamide,
- (−)p-[(4aR*,10bS*)-9-ethoxy-1,2,3,4,4a,10b-hexahydro-8-methoxy-2-methylbenzo[s]-[1,6]naphthyridin-6-yl]-N,N-diisopropylbenzamide,
- (R)-(+)-1-(4-bromobenzyl)-4-[(3-cyclopentyloxy)-4-methoxyphenyl]-2-pyrrolidone,
- 3-(cyclopentyloxy-4-methoxyphenyl)-1-(4-N'-[N-2-cyano-5-methyl-isothioureido]-benzyl)-2-pyrrolidone,
- cis[4-cyano-4-(3-cyclopentyloxy-4-methoxyphenyl)cyclohexane-1-carboxylic acid],
- 2-carbomethoxy-4-cyano-4-(3-cyclopropylmethoxy-4-difluoromethoxyphenyl)-cyclohexan-1-one,
- cis[4-cyano-4-(3-cyclopropylmethoxy-4-difluoromethoxyphenyl)cyclohexan-1-ol],
- (R)-(+)-ethyl[4-(3-cyclopentyloxy-4-methoxyphenyl)pyrrolidin-2-ylidene]acetate,
- (S)-(−)-ethyl[4-(3-cyclopentyloxy-4-methoxyphenyl)pyrrolidin-2-ylidene]acetate,
- 9-cyclopentyl-5,6-dihydro-7-ethyl-3-(2-thienyl)-9H-pyrazolo[3,4-c]-1,2,4-triazolo-[4.3-a]pyridine and
- 9-cyclopentyl-5,6-dihydro-7-ethyl-3-(tert-butyl)-9H-pyrazolo[3,4-c]-1,2,4-triazolo-[4.3-a]pyridine, optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

EGFR-inhibitors used according to the invention are preferably compounds selected from among cetuximab, trastuzumab, panitumumab (=ABX-EGF), Mab ICR-62, gefitinib, canertinib and erlotinib or

- 4-[(3-chloro-4-fluorophenyl)amino]-6-{[4-(morpholin-4-yl)-1-oxo-2-buten-1-yl]amino}-7-cyclopropylmethoxy-quinazoline,
- 4-[(3-chloro-4-fluorophenyl)amino]-6-{[4-(N,N-diethylamino)-1-oxo-2-buten-1-yl]amino}-7-cyclopropylmethoxy-quinazoline,
- 4-[(3-chloro-4-fluorophenyl)amino]-6-{[4-(N,N-dimethylamino)-1-oxo-2-buten-1-yl]amino}-7-cyclopropylmethoxy-quinazoline,
- 4-[(R)-(1-phenyl-ethyl)amino]-6-{[4-(morpholin-4-O-1-oxo-2-buten-1-yl]amino}-7-cyclopentyloxy-quinazoline,
- 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline,
- 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline,
- 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline,
- 4-[(3-chloro-4-fluoro-phenyl)amino]-6-[2-((S)-6-methyl-2-oxo-morpholin-4-yl)-ethoxy]-7-methoxy-quinazoline,
- 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)-amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert-butyloxycarbonyl)-piperidin-4-yloxy]-7-methoxy-quinazoline, 4-[(3-chloro-4-fluoro-phenyl)amino]-6-(trans-4-aminocyclohexane-1-yloxy)-7-methoxy-quinazoline, 4-[(3-chloro-4-fluoro-phenyl)amino]-6-(trans-4-methanesulphonylamino-cyclohexane-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexane-1-yloxy}-7-methoxy-quinazoline, 4-[(3-chloro-4-fluoro-phenyl)amino]-6-{trans-4-[(morpholin-4-yl)carbonylamino]-cyclohexane-1-yloxy}-7-methoxy-quinazoline, 4-[(3-chloro-4-fluoro-phenyl)amino]-6-{trans-4-[(morpholin-4-yl)sulphonylamino]-cyclohexane-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexane-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexane-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexane-1-yloxy)-7-methoxy-quinazoline, 4-[(3-chloro-4-fluoro-phenyl)amino]-6-(trans-4-ethansulphonylamino-cyclohexane-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline,
4-[(3-chloro-4-fluoro-phenyl)amino]-6-(cis-4-acetylamino-cyclohexane-1-yloxy)-7-methoxy-quinazoline,
4-[(3-ethynyl-phenyl)amino]-6-[1-(tert-butyloxycarbonyl)-piperidin-4-yloxy]-7-methoxy-quinazoline,
4-[(3-ethynyl-phenyl)amino]-6-(tetrahydropyran-4-yloxy]-7-methoxy-quinazoline,
4-[(3-chloro-4-fluoro-phenyl)amino]-6-(cis-4-{N-[(piperidin-1-yl)carbonyl]-N-methyl-amino}-cyclohexane-1-yloxy)-7-methoxy-quinazoline,
4-[(3-chloro-4-fluoro-phenyl)amino]-6-(cis-4-{N-[(4-methyl-piperazin-1-yl)carbonyl]-N-methyl-amino}-cyclohexane-1-yloxy)-7-methoxy-quinazoline,
4-[(3-chloro-4-fluoro-phenyl)amino]-6-{cis-4-[(morpholin-4-yl)carbonylamino]-cyclohexane-1-yloxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-chloro-4-fluoro-phenyl)amino]-6-{1-[(morpholin-4-yl)carbonyl]-piperidin-4-yloxy}-7-(2-methoxy-ethoxy)-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-chloro-4-fluoro-phenyl)amino]-6-(1-methyl-piperidin-4-yloxy)-7(2-methoxy-ethoxy)-quinazoline,
4-[(3-chloro-4-fluoro-phenyl)amino]-6-(1-isopropyloxycarbonyl-piperidin-4-yloxy)-7-methoxy-quinazoline,
4-[(3-chloro-4-fluoro-phenyl)amino]-6-(cis-4-methylamino-cyclohexane-1-yloxy)-7-methoxy-quinazoline,
4-[(3-chloro-4-fluoro-phenyl)amino]-6-{cis-4-N-(2-methoxy-acetyl)-N-methyl-amino]-cyclohexane-1-yloxy}-7-methoxy-quinazoline,
4-[(3-ethynyl-phenyl)amino]-6-(piperidin-4-yloxy)-7-methoxy-quinazoline,
4-[(3-ethynyl-phenyl)amino]-6-[1-(2-methoxy-acetyl)-piperidin-4-yloxy]-7-methoxy-quinazoline,
4-[(3-ethynyl-phenyl)amino]-6-{1-[(morpholin-4-yl)carbonyl]piperidin-4-yloxy}-7-methoxy-quinazoline,
4-[(3-chloro-4-fluoro-phenyl)amino]-6-{1-[(cis-2,6-dimethyl-morpholin-4-yl)carbonyl]-piperidin-4-yloxy}-7-methoxy-quinazoline,
4-[(3-chloro-4-fluoro-phenyl)amino]-6-{1-[(2-methyl-morpholin-4-yl)carbonyl]-piperidin-4-yloxy}-7-methoxy-quinazoline,
4-[(3-chloro-4-fluoro-phenyl)amino]-6-{1-[(S,S)-(2-oxa-5-aza-bicyclo[2,2,1]hept-5-yl)-carbonyl]piperidin-4-yloxy}-7-methoxy-quinazoline,
4-[(3-chloro-4-fluoro-phenyl)amino]-6-{1-[(N-methyl-N-2-methoxyethyl-amino)carbonyl]piperidin-4-yloxy}-7-methoxy-quinazoline,
4-[(3-chloro-4-fluoro-phenyl)amino]-6-(1-ethyl-piperidin-4-yloxy)-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-{1-[(3-methoxypropyl-amino)-carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexane-1-yloxy]-7-methoxy-quinazoline,
4-[(3-chloro-4-fluoro-phenyl)amino]-6-[cis-4-(N-acetyl-N-methyl-amino)-cyclohexane-1-yloxy]-7-methoxy-quinazoline,
4-[(3-chloro-4-fluoro-phenyl)amino]-6-(trans-4-methylamino-cyclohexane-1-yloxy)-7-methoxy-quinazoline,
4-[(3-chloro-4-fluoro-phenyl)amino]-6-[trans-4-(N-methanesulphonyl-N-methyl-amino)-cyclohexane-1-yloxy]-7-methoxy-quinazoline,
4-[(3-chloro-4-fluoro-phenyl)amino]-6-(trans-4-dimethylamino-cyclohexane-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexane-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline,
4-[(3-chloro-4-fluoro-phenyl)amino]-6-(1-cyano-piperidin-4-yloxy)-7-methoxy-quinazoline,
3-cyano-4-[(3-chloro-4-fluorophenyl)amino]-6-{[4-(N,N-dimethylamino)-1-oxo-2-buten-1-yl]amino}-7-ethoxy-quinoline;
[4-[(3-chloro-4-fluorophenyl)amino]-6-{[4-(homomorpholin-4-yl)-1-oxo-2-buten-1-yl]-amino}-7-[(S)-(tetrahydrofuran-3-yl)oxy]-quinazoline,
4-[(3-chloro-4-fluorophenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline,
4-[(3-chloro-4-fluorophenyl)amino]-7-[2-((S)-6-methyl-2-oxo-morpholin-4-yl)-ethoxy]-6-[(vinylcarbonyl)amino]-quinazoline,
4-[(3-chloro-4-fluorophenyl)amino]-7-[4-((R)-6-methyl-2-oxo-morpholin-4-yl)-butyloxy]-6-[(vinylcarbonyl)amino]-quinazoline,
4-[(3-chloro-4-fluorophenyl)amino]-7-[4-((S)-6-methyl-2-oxo-morpholin-4-yl)-butyloxy]-6-[(vinylcarbonyl)amino]-quinazoline, and
4-[(3-chloro-4-fluorophenyl)amino]-6-[(4-{N-[2-(ethoxycarbonyl)-ethyl]-N-[(ethoxy-carbonyl)methyl]amino}-1-oxo-2-buten-1-yl)amino]-7-cyclopropylmethoxy-quinazoline, optionally in the form of their racemates, enantiomers or diastereomers, optionally in the form of the pharmacologically acceptable acid addition salts, solvates and/or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used according to the invention are preferably compounds selected from among montelukast, pranlukast and zafirlukast, or (E)-8-[2-[4-[4-(4-fluorophenyl)butoxy]phenyl]ethenyl]-2-(1H-tetrazol-5-yl)-4H-1-benzopyran-4-one (MEN-91507),
  4-[6-acetyl-3-[3-(4-acetyl-3-hydroxy-2-propylphenylthio)propoxy]-2-propylphenoxy]-butyric acid (MN-001),
  1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid and

[2-[[2-(4-tert-butyl-2-thiazolyl)-5-benzofuranyl]oxymethyl]phenyl]acetic acid, optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-receptor antagonists may optionally be capable of forming are meant, for example: alkali metal salts, such as for example sodium or potassium salts, alkaline earth salts, sulphobenzoates, phosphates, isonicotinates, acetates, propionates, dihydrogen phosphates, palmitates, pivalates or furoates.

Histamine H1 receptor antagonists used according to the invention are preferably compounds selected from among epinastin, cetirizin, azelastin, fexofenadin, levocabastin, loratadin, mizolastin, ketotifen, emedastin, dimetinden, clemastin, bamipin, cexchlorpheniramin, pheniramin, doxylamine, chlorophenoxamin, dimenhydrinat, diphenhydramin, promethazin, ebastin, olopatadine, desloratidin and meclozin, optionally in the form of their racemates, enantiomers, diastereomers and optionally in the form of the pharmacologically acceptable acid addition salts, solvates or hydrates thereof. Preferably, according to the invention, the acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists used according to the invention are preferably compounds such as for example (5-chloro-1H-indol-2-yl)-(4-methyl-1-piperazinyl)-methanone (JNJ-7777120), optionally in the form of their racemates, enantiomers, diastereomers and optionally in the form of the pharmacologically acceptable acid addition salts, solvates or hydrates thereof. Preferably, according to the invention, acid addition salts selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate are used.

MAP Kinase inhibitors used according to the invention are preferably compounds selected from among:

Bentamapimod (AS-602801)
Doramapimod,
5-carbamoylindole (SD-169),
6-[(aminocarbonyl)(2,6-difluorophenyl)amino]-2-(2,4-difluorophenyl)-3-pyridinecarboxamide (VX-702),
alpha-[2-[[2-(3-pyridinyl)ethyl]amino]-4-pyrimidinyl]-2-benzothiazoleacetonitrile (AS-601245),
9,12-epoxy-1H-diindolo[1,2,3-fg:3'.2'.1'-kl]pyrrolo[3,4-i][1.6]benzodiazocine-10-carboxylic acid (CEP-1347), and
4-[3-(4-chlorophenyl)-5-(1-methyl-4-piperidinyl)-1H-pyrazol-4-yl]-pyrimidine (SC-409), optionally in the form of their racemates, enantiomers, diastereomers and optionally in the form of the pharmacologically acceptable acid addition salts, prodrugs, solvates or hydrates thereof.

Neurokinin (NK1 or NK2) antagonists used according to the invention are preferably compounds selected from among: Saredutant, Nepadutant and Figopitant, optionally in the form of their racemates, enantiomers, diastereomers and optionally in the form of the pharmacologically acceptable acid addition salts, prodrugs, solvates or hydrates thereof.

Antitussive substances used according to the invention are preferably compounds selected from among hydrocodone, caramiphen, carbetapentane and dextramethorphane, optionally in the form of their racemates, enantiomers, diastereomers and optionally in the form of the pharmacologically acceptable acid addition salts, prodrugs, solvates or hydrates thereof.

Substances of preferred CXCR1 or CXCR2 antagonists used according to the invention are preferably compounds such as e.g. 3-[[3-[(dimethylamino)carbonyl]-2-hydroxyphenyl]amino]-4-[[(R)-1-(5-methylfuran-2-yl)propyl]amino]cyclobut-3-ene-1,2-dione (SCH-527123), optionally in the form of its racemates, enantiomers, diastereomers and optionally in the form of its pharmacologically acceptable acid addition salts, prodrugs, solvates or hydrates.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case one to three times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

EXPERIMENTAL SECTION

Generally, there are mass spectra and $^1$H NMR spectra for the compounds that have been prepared. The ratios given for the eluants are in volume units of the solvents in question. For ammonia, the given volume units are based on a concentrated solution of ammonia in water.

Unless indicated otherwise, the acid, base and salt solutions used for working up the reaction solutions are aqueous systems having the stated concentrations.

For chromatographic purification, silica gel from Millipore (MATREX™, 35 to 70 µm) or Alox (E. Merck, Darmstadt, Alumina 90 standardized, 63 to 200 µm, article No. 1.01097.9050) is used.

In the descriptions of the experiments, the following abbreviations are used:
TLC thin layer chromatograph
DMSO dimethylsulphoxide
RP reverse phase
$R_t$ retention time
tert tertiary
TBTU 2-(1H-benzotriazol-1-yl)-1,1,3,3-tetramethyluronium-tetrafluoroborate
THF tetrahydrofuran The following analytical HPLC methods were used:

Method 1:

| | |
|---|---|
| Column: | Interchim Strategy C18, 5 µM, 4.6 × 50 mm |
| Detection: | 220-320 nm |
| Eluant A: | water/0.1% acetic acid |
| Eluant B: | acetonitrile |
| Gradient: | |

| time in min | % A | % B | flow rate in mL/min |
|---|---|---|---|
| 0.0 | 95.0 | 5.0 | 3.0 |
| 0.3 | 95.0 | 5.0 | 3.0 |
| 2.0 | 2.0 | 98.0 | 3.0 |
| 2.4 | 2.0 | 98.0 | 3.0 |
| 2.45 | 95.0 | 5.0 | 3.0 |
| 2.8 | 95.0 | 5.0 | 3.0 |

Method 2:

| | |
|---|---|
| Column: | Merck Cromolith Flash RP18e, 4.6 × 25 mm |
| Eluant A: | water/0.1% formic acid |
| Eluant B: | acetonitrile/0.1% formic acid |
| Gradient: | |

| time in min | % A | % B | flow rate in mL/min |
|---|---|---|---|
| 0.0 | 90.0 | 10.0 | 1.6 |
| 2.7 | 10.0 | 90.0 | 1.6 |
| 3.0 | 10.0 | 90.0 | 1.6 |
| 3.3 | 90.0 | 10.0 | 1.6 |

Method 3:

| | |
|---|---|
| Column: | YMC-Pack ODS-AQ, 3 µM, 4.6 × 75 mm |
| Eluant A: | water/0.15% formic acid |
| Eluant B: | acetonitrile |
| Gradient: | |

| time in min | % A | % B | flow rate in mL/min |
|---|---|---|---|
| 0.0 | 95.0 | 5.0 | 1.6 |
| 2.0 | 10.0 | 90.0 | 1.6 |
| 5.0 | 10.0 | 90.0 | 1.6 |
| 5.5 | 90.0 | 10.0 | 1.6 |

Method 4:

| | |
|---|---|
| Column: | Zorbax Stable Bond C18, 1.8 µM, 3 × 30 mm |
| Eluant A: | water/0.15% formic acid |
| Eluant B: | acetonitrile |
| Gradient: | |

| time in min | % A | % B | flow rate in mL/min |
|---|---|---|---|
| 0.0 | 95.0 | 5.0 | 1.6 |
| 1.0 | 10.0 | 90.0 | 1.6 |
| 2.5 | 10.0 | 90.0 | 1.6 |
| 2.75 | 95.0 | 5.0 | 1.6 |

Method 5:

| | |
|---|---|
| Column: | Sunfire C18, 3.5 µM, 4.6 × 50 mm |
| Detection: | 180-820 nm |
| Eluant A: | water/0.1% trifluoroacetic acid |
| Eluant B: | acetonitrile/0.1% trifluoroacetic acid |
| Temperature: | 40° C. |
| Gradient: | |

| time in min | % A | % B | flow rate in mL/min |
|---|---|---|---|
| 0.0 | 95.0 | 5.0 | 1.5 |
| 2.0 | 0.0 | 100.0 | 1.5 |
| 2.5 | 0.0 | 100.0 | 1.5 |
| 2.6 | 95.0 | 5.0 | 1.5 |

Method 6:

| | |
|---|---|
| Column: | Sunfire C18, 3.5 µM, 4.6 × 50 mm |
| Detection: | 180-820 nm |
| Eluant A: | water/0.1% trifluoroacetic acid |
| Eluant B: | acetonitrile 0.1% trifluoroacetic acid |
| Temperature: | 40° C. |
| Gradient: | |

| time in min | % A | % B | flow rate in mL/min |
|---|---|---|---|
| 0.0 | 95.0 | 5.0 | 1.5 |
| 2.0 | 0.0 | 100.0 | 1.5 |
| 3.0 | 0.0 | 100.0 | 1.5 |
| 3.4 | 95.0 | 5.0 | 1.5 |

Method 7:

| | |
|---|---|
| Column: | YMC-Pack ODS-AQ, 3 µM, 4.6 × 75 mm |
| Eluant A: | water/0.15% formic acid |
| Eluant B: | acetonitrile |
| Gradient: | |

| time in min | % A | % B | flow rate in mL/min |
|---|---|---|---|
| 0.0 | 95.0 | 5.0 | 1.6 |
| 4.5 | 10.0 | 90.0 | 1.6 |
| 5.0 | 10.0 | 90.0 | 1.6 |
| 5.50 | 90.0 | 10.0 | 1.6 |

Method 8:

| | |
|---|---|
| Column: | Zorbax Stable Bond C18, 1.8 µM, 3 × 30 mm |
| Eluant A: | water/0.15% formic acid |
| Eluant B: | acetonitrile |
| Gradient: | |

| time in min | % A | % B | flow rate in mL/min |
|---|---|---|---|
| 0.0 | 95.0 | 5.0 | 1.6 |
| 2.00 | 50.0 | 50.0 | 1.6 |
| 2.25 | 10.0 | 90.0 | 1.6 |
| 2.50 | 10.0 | 90.0 | 1.6 |
| 2.75 | 95.0 | 5.0 | 1.6 |

Method 9:

Column: Zorbax Stable Bond C18, 1.8 μM, 3 × 30 mm
Eluant A: water/0.15% formic acid
Eluant B: acetonitrile
Gradient:

| time in min | % A | % B | flow rate in mL/min |
| --- | --- | --- | --- |
| 0.0 | 95.0 | 5.0 | 1.6 |
| 2.25 | 10.0 | 90.0 | 1.6 |
| 2.50 | 10.0 | 90.0 | 1.6 |
| 2.75 | 95.0 | 5.0 | 1.6 |

Method 10:

Column: Zorbax Stable Bond C18, 3.5 μM, 4.6 × 75 mm
Eluant A: water/0.15% formic acid
Eluant B: acetonitrile
Gradient:

| time in min | % A | % B | flow rate in mL/min |
| --- | --- | --- | --- |
| 0.0 | 95.0 | 5.0 | 1.6 |
| 4.5 | 10.0 | 90.0 | 1.6 |
| 5.0 | 10.0 | 90.0 | 1.6 |
| 5.50 | 90.0 | 10.0 | 1.6 |

Method 11:

Column: X Terra C18, 3.5 μM, 4.6 × 50 mm
Detection: 180-820 nm
Eluant A: water/0.1% trifluoroacetic acid
Eluant B: acetonitrile/0.1% trifluoroacetic acid
Temperature: 40° C.
Gradient:

| time in min | % A | % B | flow rate in mL/min |
| --- | --- | --- | --- |
| 0.0 | 95.0 | 5.0 | 1.5 |
| 2.0 | 0.0 | 100.0 | 1.5 |
| 3.0 | 0.0 | 100.0 | 1.5 |
| 3.4 | 95.0 | 5.0 | 1.5 |

Method 12:

Column: Merck Cromolith Flash RP18e, 4.6 × 25 mm
Eluant A: water/0.1% formic acid
Eluant B: acetonitrile/0.1% formic acid
Gradient:

| time in min | % A | % B | flow rate in mL/min |
| --- | --- | --- | --- |
| 0.0 | 90.0 | 10.0 | 1.6 |
| 2.7 | 10.0 | 90.0 | 1.6 |
| 3.0 | 10.0 | 90.0 | 1.6 |
| 3.3 | 95.0 | 5.0 | 1.6 |

Method 13:

Column: Merck Cromolith SpeedROD RP-18e, 4.6 × 50 mm
Eluant A: water/0.1% formic acid
Eluant B: acetonitrile/0.1% formic acid
Gradient:

| time in min | % A | % B | flow rate in mL/min |
| --- | --- | --- | --- |
| 0.0 | 90.0 | 10.0 | 1.5 |
| 4.5 | 10.0 | 90.0 | 1.5 |
| 5.0 | 10.0 | 90.0 | 1.5 |
| 5.5 | 95.0 | 5.0 | 1.5 |

Method 14:

Column: Zorbax Stable Bond C18, 3.5 μM, 4.6 × 75 mm
Eluant A: water/0.15% formic acid
Eluant B: acetonitrile
Gradient:

| time in min | % A | % B | flow rate in mL/min |
| --- | --- | --- | --- |
| 0.0 | 95.0 | 5.0 | 1.6 |
| 2.0 | 10.0 | 90.0 | 1.6 |
| 5.0 | 10.0 | 90.0 | 1.6 |
| 5.5 | 90.0 | 10.0 | 1.6 |

The following preparative methods were used for the reversed-phase chromatography:

Method 1:

Column: Atlantis C18, 5 μM, 100 × 30 mm
Detection: 210-500 nm
Eluant A: water/0.1% trifluoroacetic acid
Eluant B: acetonitrile
Gradient:

| time in min | % A | % B | flow rate in mL/min |
| --- | --- | --- | --- |
| 0.0 | 95.0 | 5.0 | 5 |
| 0.5 | 95.0 | 5.0 | 50 |
| 8.0 | 5.0 | 95.0 | 50 |
| 9.0 | 5.0 | 95.0 | 50 |
| 9.5 | 95.0 | 5.0 | 50 |
| 10.0 | 95.0 | 5.0 | 50 |
| 10.1 | 95.0 | 5.0 | 5 |

Method 2:

Column: Varian Pursuit 5 μM, 50 × 200 mm
Eluant A: water/0.1% trifluoroacetic acid
Eluant B: acetonitrile/0.1% trifluoroacetic acid
Gradient:

| time in min | % A | % B | flow rate in mL/min |
| --- | --- | --- | --- |
| 0.0 | 95.0 | 5.0 | 180 |
| 1.15 | 95.0 | 5.0 | 180 |
| 12.4 | 2.0 | 98.0 | 180 |
| 14.0 | 2.0 | 98.0 | 180 |
| 15.3 | 95.0 | 5.0 | 180 |
| 15.3 | 95.0 | 5.5 | 180 |

| Method 3: | | | |
|---|---|---|---|
| Column: | YMC-Pack ODS-AQ 5 μM, 30 × 100 mm | | |
| Eluant A: | water/0.15% formic acid | | |
| Eluant B: | acetonitrile | | |
| Gradient: | | | |
| time in min | % A | % B | flow rate in mL/min |
| 0.0 | 95.0 | 5.0 | 50 |
| 2.0 | 95.0 | 5.0 | 50 |
| 6.0 | 10.0 | 90.0 | 50 |
| 12.0 | 10.0 | 90.0 | 50 |
| 13 | 90.0 | 10.0 | 50 |

Preparation of the Starting Compounds

The compounds of general formula I may be prepared from the following intermediates A, B and C:

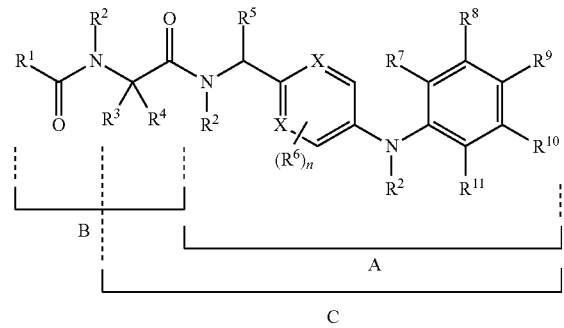

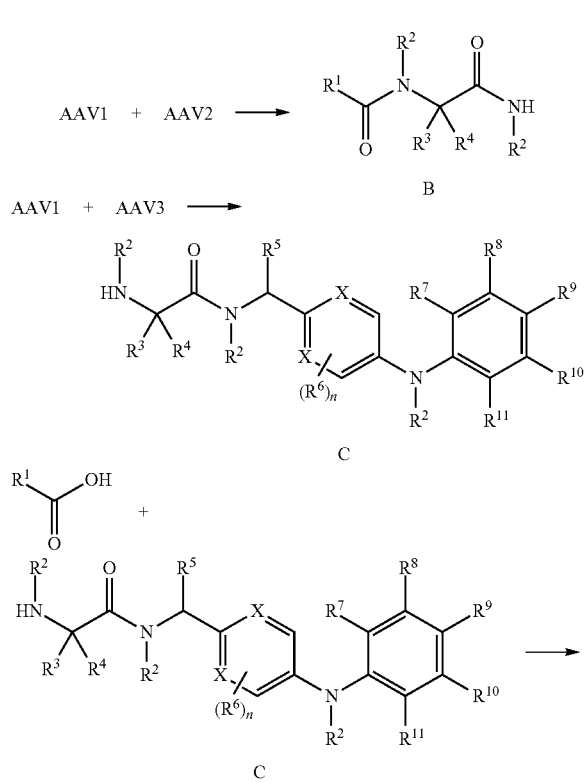

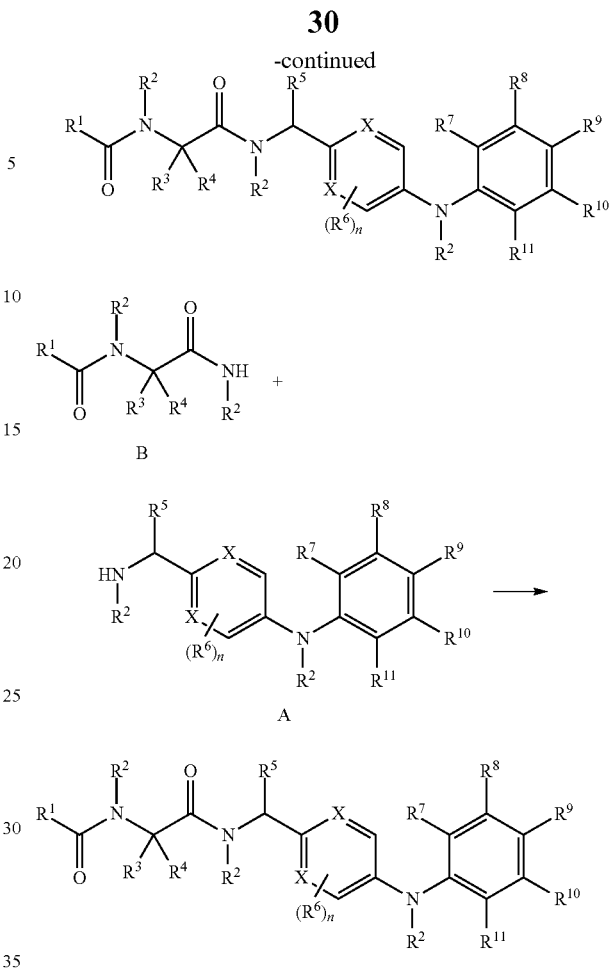

AAV 1: Amide Coupling

A solution of the carboxylic acid component (1 mol-equivalent), triethylamine (2.5 mol-equivalents) and TBTU (1.1 mol-equivalents) in THF was stirred for 30 minutes at ambient temperature. Then the amine component (1.1 mol-equivalent as hydrochloride) was added and stirring was continued overnight. Then the mixture was evaporated down, mixed with water, made alkaline with dilute potassium carbonate solution and extracted with ethyl acetate. The product was isolated and purified by column chromatography (either silica gel or reversed phase chromatography).

AAV 2: Ester Hydrolysis 2N sodium hydroxide solution (2 mol-equivalents) was added to a solution of the ester (1 mol-equivalent) in methanol and the mixture was stirred for 1 to 5 hours at ambient temperature. Then it was acidified with acetic acid and the mixture was evaporated to dryness in vacuo. The crude product thus obtained was purified in the normal way by column chromatography on silica gel.

AAV 3: Cleaving the Tert-Butyloxycarbonyl Protective Group

A solution of the tert-butoxycarbonyl-amino compound (1 mol-equivalent) in dichloromethane was combined with trifluoroacetic acid (3 to 10 mol-equivalents) and stirred at ambient temperature until the protective group had been cleaved completely. The reaction mixture was then evaporated to dryness and the crude product thus obtained was purified by chromatography.

AAV 4: Preparation of the Intermediate A

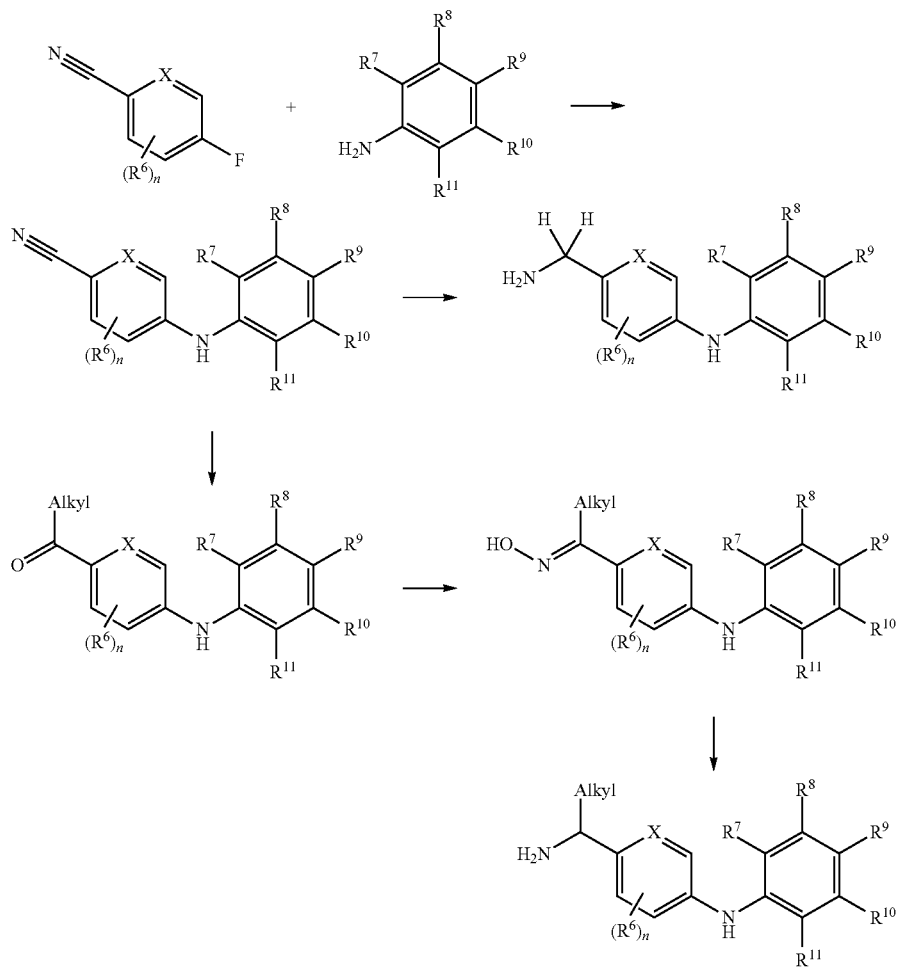

A solution of the aniline component (1 mol-equivalent) and a strong base such as e.g. potassium-tert-butoxide (1 mol-equivalent) in DMSO was stirred for one hour at ambient temperature, then combined with the 4-fluoro-benzonitrile component (1 mol-equivalent) and stirred overnight at approx. 80° C. For working up the mixture was filtered through Alox and evaporated to dryness in vacuo.

The nitrile group of the diphenylamine intermediate product thus obtained was then reduced to the aminomethyl group with the addition of Raney nickel at 55° C. and 3 bar excess hydrogen pressure and the product obtained was purified by chromatography. In order to prepare the intermediate A with an alpha-alkylbenzyl group (e.g. A1, A4, A5) the nitrile derivative (1 mol-equivalent) was dissolved in diethyl ether and at 0 to 5° C. it was added with stirring to a solution of alkylmagnesium bromide (4 mol-equivalents) in diethyl ether and then stirred for another 30 minutes approx. The reaction mixture was then stirred into 1M hydrochloric acid at −5° C. and the alkylketone thus obtained was isolated and purified by chromatography in the usual way.

A solution of the ketone thus obtained (1 mol-equivalent) in acetonitrile was combined with triethylamine (2 mol-equivalents) and hydroxylamine-hydrochloride (1.3 mol-equivalents) and refluxed for 4 hours. Then water was added and the mixture was extracted with dichloromethane. The resulting oxime was isolated from the organic phase and purified by conventional methods.

A solution of the oxime (1 mol-equivalent) in methanol was combined with methanolic hydrochloric acid (6.6 mol-equivalents). After the addition of zinc powder (1.4 mol-equivalents) the mixture was refluxed for 3 hours with stirring. After cooling the mixture was combined with water and extracted with dichloromethane. If necessary, the amine thus obtained was purified by chromatography.

Another possible way of reducing the oxime to the corresponding amine is by catalytic hydrogenation. For this, the oxime was hydrogenated in methanolic ammonia solution after the addition of Raney nickel at 50° C. and at an excess hydrogen pressure of 50 psi until the uptake of hydrogen had ended. If necessary, the amine thus obtained was purified by chromatography.

Preparation of the Intermediates A

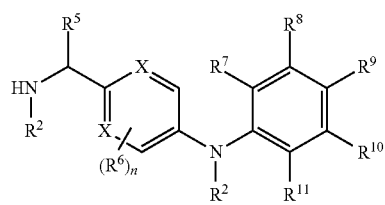

The following intermediates A1 to A31 were prepared according to general working method AAV4:

Intermediate A1

(6-aminomethyl-pyridin-3-yl)-(4-chloro-2-trifluoromethyl-phenyl)-<amine

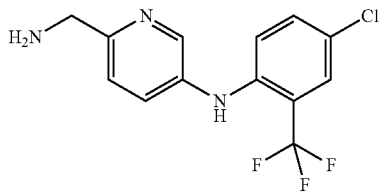 [SMILES: NCc1ccc(Nc2ccc(Cl)cc2C(F)(F)F)cn1]

HPLC: $R_t$=1.74 minutes (method 13)
Mass spectrum (ESI): [M+H]+=302

Intermediate A2

(4-aminomethyl-phenyl)-(4-fluoro-2-trifluoromethyl-phenyl)-amine

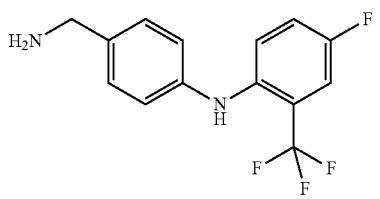 [SMILES: NCc1ccc(Nc2ccc(F)cc2C(F)(F)F)cc1]

Mass spectrum (ESI): [M+H]+=285
thin layer chromatogram (silica gel, $CH_2Cl_2$/ethanol 19:1): $R_f$=0.16

Intermediate A3

(6-aminomethyl-pyridin-3-yl)-(4-fluoro-2-trifluoromethyl-phenyl)-amine

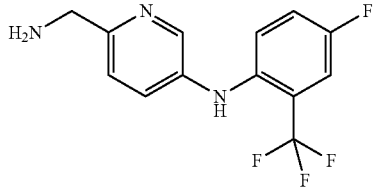 [SMILES: NCc1ccc(Nc2ccc(F)cc2C(F)(F)F)cn1]

HPLC: $R_t$=2.06 minutes (method 3)
Mass spectrum (ESI): [M+H]+=286; [M−H]−=284

Intermediate A4

(4-aminomethyl-3-fluoro-phenyl)-(4-fluoro-2-trifluoromethyl-phenyl)-amine

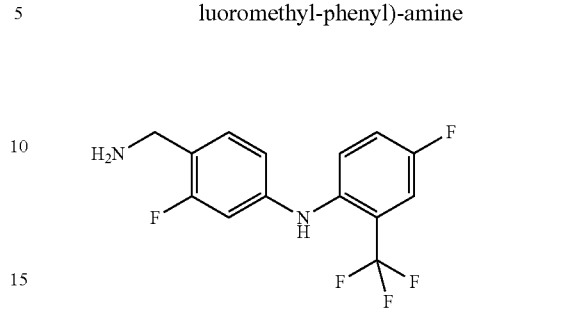

Mass spectrum (ESI): [M+H]+=303
thin layer chromatogram (silica gel, $CH_2Cl_2$/ethanol 19:1): $R_f$=0.08

Intermediate A5

(4-aminomethyl-3-fluoro-phenyl)-(2-trifluoromethyl-phenyl)-amine

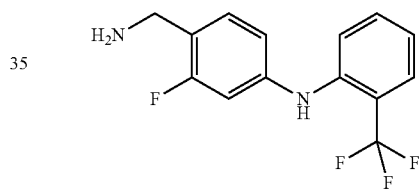

Mass spectrum (ESI): [M−H]−=283
thin layer chromatogram (silica gel, $CH_2Cl_2$/ethanol 19:1): $R_1$=0.09

Intermediate A6

(4-aminomethyl-phenyl)-(2-trifluoromethyl-phenyl)-amine

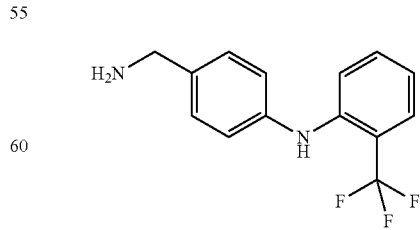

HPLC: $R_t$=1.36 minutes (method 1)
Mass spectrum (ESI): [M+H—$NH_3$]+=250

Intermediate A7

(4-aminomethyl-phenyl)-(4-chloro-2-trifluoromethyl-phenyl)-amine

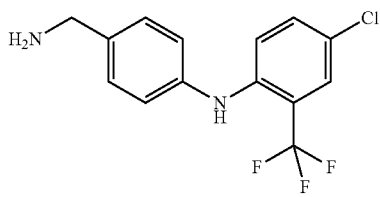 [SMILES: NCc1ccc(Nc2ccc(Cl)cc2C(F)(F)F)cc1]

Mass spectrum (ESI): [M+H—NH$_3$]+=284/286

Intermediate A8

(4-aminomethyl-3-fluoro-phenyl)-(4-chloro-2-trifluoromethyl-phenyl)-amine

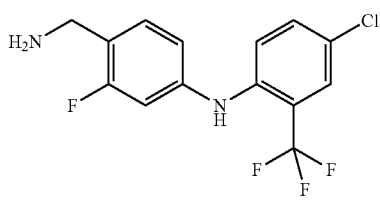 [SMILES: NCc1ccc(Nc2ccc(Cl)cc2C(F)(F)F)cc1F]

HPLC: R$_t$=1.83 minutes (method 2)

Intermediate A9

(4-aminomethyl-phenyl)-(4-bromo-2-trifluoromethyl-phenyl)-amine

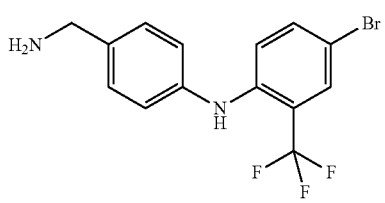 [SMILES: NCc1ccc(Nc2ccc(Br)cc2C(F)(F)F)cc1]

HPLC: R$_t$=1.81 minutes (method 2)

Preparation of the Intermediates B

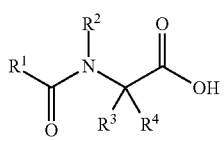

The following Intermediate B1 was prepared by amide coupling according to general working method AAV1 and subsequent ester saponification according to general working method AAV2:

Intermediate B1

(S)-3-[(6-oxo-1,6-dihydro-pyridazine-4-carbonyl)-amino]-tetrahydro-furan-3-carboxylic acid

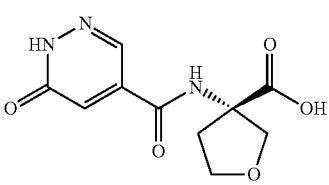 [SMILES: O=C(N[C@@]1(C(=O)O)CCOC1)c1cn[nH]c(=O)c1]

HPLC: R$_t$=0.33 minutes (method 2)
Mass spectrum (ESI): [M+H]+=254

The following Intermediate B2 may be prepared analogously:

Intermediate B2

1-[(6-oxo-1,6-dihydro-pyridazine-4-carbonyl)-amino]-cyclopropanecarboxylic acid

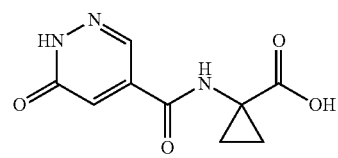 [SMILES: O=C(NC1(C(=O)O)CC1)c1cn[nH]c(=O)c1]

Preparation of the Intermediates C

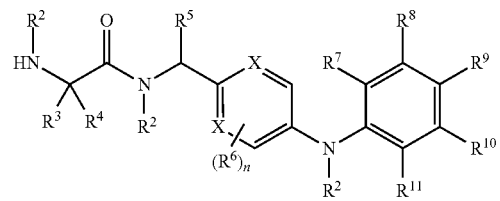

The following Intermediates C1 to C6 were prepared by amide coupling according to general working method AAV1 and subsequent cleaving of the tert-butyloxycarbonyl-protective group according to general working method AAV3:

Intermediate C1

1-amino-cyclopropanecarboxylic acid-[5-(4-chloro-2-trifluoromethyl-phenylamino)-pyridin-2-ylmethyl]-amide

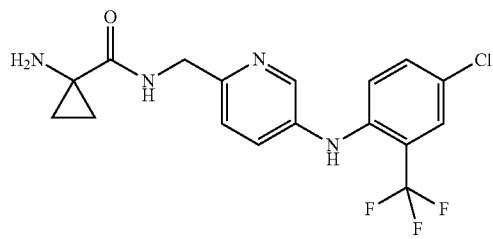 [SMILES: NC1(C(=O)NCc2ccc(Nc3ccc(Cl)cc3C(F)(F)F)cn2)CC1]

HPLC: $R_t$=1.55 minutes (method 13)
Mass spectrum (ESI): [M−H]−=383

Intermediate C2

1-amino-cyclopropanecarboxylic acid-[5-(4-fluoro-2-trifluoromethyl-phenylamino)-pyridin-2-ylmethyl]-amide

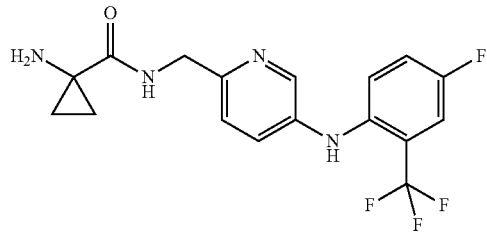 [SMILES: NC1(C(=O)NCc2ccc(Nc3ccc(F)cc3C(F)(F)F)cn2)CC1]

HPLC: $R_t$=2.33 minutes (method 7)
Mass spectrum (ESI): [M+H]+=369; [M−H]−=367

Intermediate C3

(S)-3-amino-tetrahydrofuran-3-carboxlic acid-2-fluoro-4-(4-fluoro-2-trifluoromethyl-phenylamino)-benzylamide

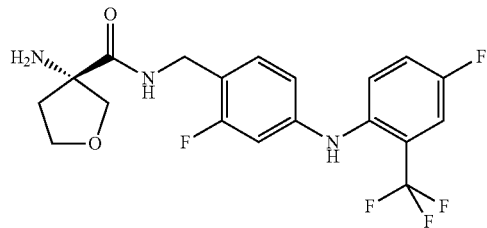 [SMILES: N[C@@]1(C(=O)NCc2ccc(Nc3ccc(F)cc3C(F)(F)F)cc2F)CCOC1]

Mass spectrum (ESI): [M+H]+=416

Intermediate C4

(S)-3-amino-tetrahydrofuran-3-carboxylic acid-4-(4-fluoro-2-trifluoromethyl-phenylamino)-benzylamide

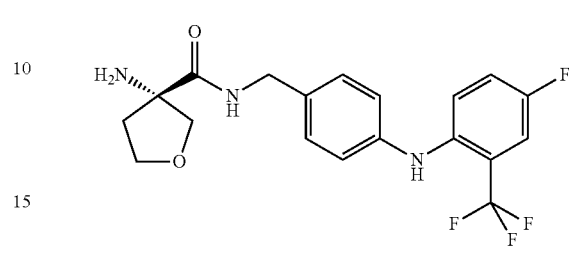

HPLC: $R_t$=1.99 minutes (method 2)
Mass spectrum (ESI): [M+H]+=398

Intermediate C5

(S)-3-amino-tetrahydrofuran-3-carboxylic acid-4-(4-chloro-2-trifluoromethyl-phenylamino)-benzylamide

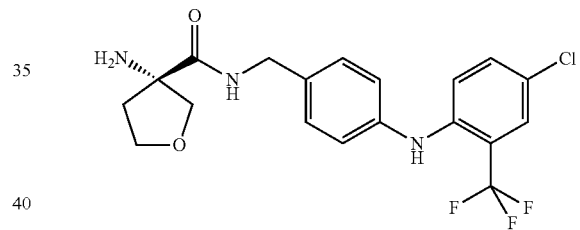

HPLC: $R_t$=2.41 minutes (method 2)

Intermediate C6

(S)-3-amino-tetrahydrofuran-3-carboxylic acid 2-fluoro-4-(2-trifluoromethyl-phenylamino)-benzylamide

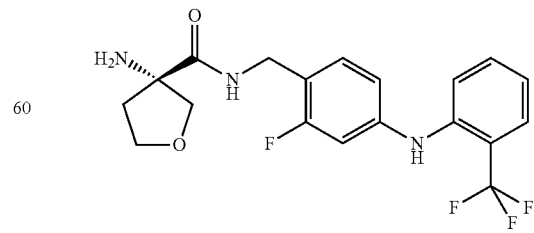

Mass spectrum (ESI): [M+H]+=398

39

Preparation of the End Compounds

EXAMPLE 1

6-oxo-5,6-dihydro-pyridazine-4-carboxylic acid-(1-{[5-(4-fluoro-2-trifluoromethyl-phenylamino)-pyridin-2-ylmethyl]-carbamoyl}-cyclopropyl)-amide

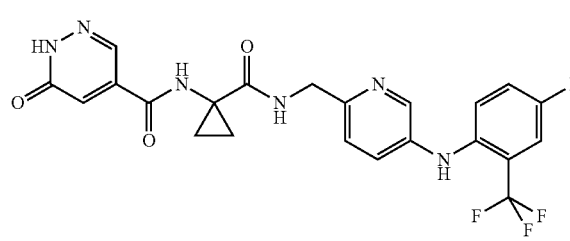

Prepared from intermediate C2 and 6-oxo-1,6-dihydro-pyridazine-4-carboxylic acid according to AAV1.
$C_{22}H_{18}F_4N_6O_3$ (490.42)
$R_t$=2.80 minutes (method 7)

EXAMPLE 2

6-oxo-1,6-dihydro-pyridazine-4-carboxylic acid-(1-{[5-(4-chloro-2-trifluoromethyl-phenylamino)-pyridin-2-ylmethyl]-carbamoyl}-cyclopropyl)-amide

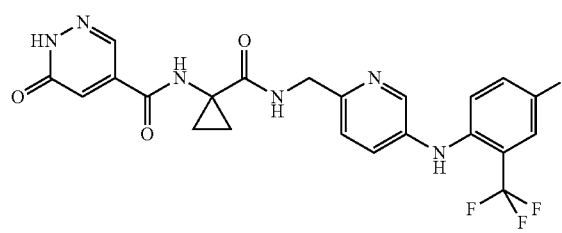

Prepared from intermediate C1 and 6-oxo-1,6-dihydro-pyridazine-4-carboxylic acid according to AAV1.
$C_{22}H_{18}ClF_3N_6O_3$ (506.87)
$R_t$=2.13 minutes (method 2)

EXAMPLE 3

(S)-6-oxo-1,6-dihydro-pyridazine-4-carboxylic acid-{3-[4-(4-fluoro-2-trifluoromethyl-phenylamino)-benzylcarbamoyl]-tetrahydrofuran-3-yl}-amide

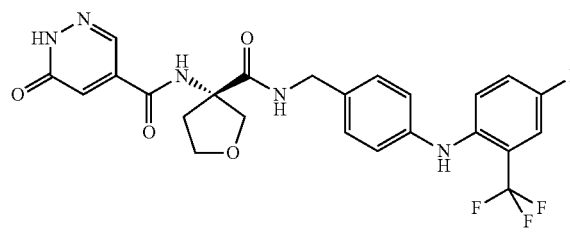

Prepared from intermediate C4 and 6-oxo-1,6-dihydro-pyridazine-4-carboxylic acid according to AAV1.
$C_{24}H_{21}F_4N_5O_4$ (519.45)
$R_t$=2.39 minutes (method 2)

40

EXAMPLE 4

(S)-6-oxo-1,6-dihydro-pyridazine-4-carboxylic acid-{3-[4-(4-chloro-2-trifluoromethyl-phenylamino)-benzylcarbamoyl]-tetrahydrofuran-3-yl}-amide

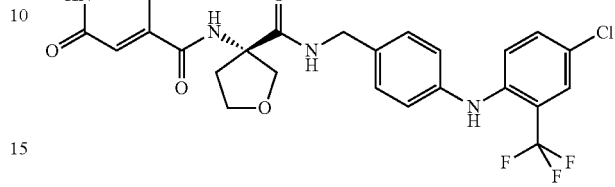

Prepared from intermediates A7 and B1 according to AAV1.
$C_{24}H_{21}ClF_3N_5O_4$ (535.91)
$R_t$=2.28 minutes (method 2)

EXAMPLE 5

(S)-6-oxo-1,6-dihydro-pyridazine-4-carboxylic acid-{3-[4-(2-trifluoromethyl-phenylamino)-benzylcarbamoyl]-tetrahydrofuran-3-yl}-amide

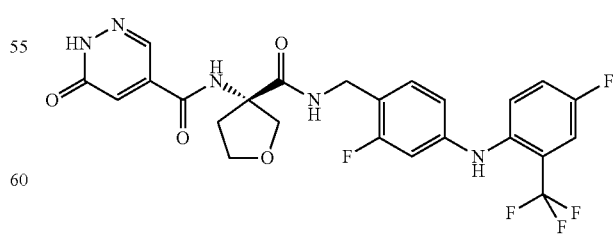

Prepared from intermediates A6 and B1 according to AAV1.
$C_{24}H_{22}F_3N_5O_4$ (501.46)
$R_t$=2.09 minutes (method 2)

EXAMPLE 6

(S)-6-oxo-1,6-dihydro-pyridazine-4-carboxylic acid-{3-[2-fluoro-4-(4-fluoro-2-trifluoromethyl-phenylamino)-benzylcarbamoyl]-tetrahydrofuran-3-yl}-amide Prepared from intermediates A4 and B1 according to AAV1.
$C_{24}H_{20}F_5N_5O_4$ (537.44)
$R_t$=2.15 minutes (method 2)

EXAMPLE 7

(S)-6-oxo-1,6-dihydro-pyridazine-4-carboxylic acid-{3-[4-(4-chloro-2-trifluoromethyl-phenylamino)-2-fluoro-benzylcarbamoyl]-tetrahydrofuran-3-yl}-amide

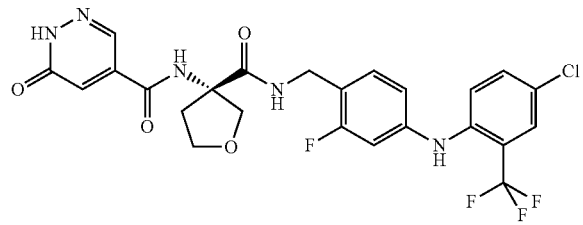 [SMILES: O=C(N[C@@]1(C(=O)NCc2ccc(Nc3ccc(Cl)cc3C(F)(F)F)cc2F)CCOC1)c1cn[nH]c(=O)c1]

Prepared from intermediates A8 and B1 according to AAV1.
$C_{24}H_{20}ClF_4N_5O_4$ (553.90)
$R_t$=2.31 minutes (method 2)

EXAMPLE 8

(S)-6-oxo-1,6-dihydro-pyridazine-4-carboxylic acid-{3-[4-(4-bromo-2-trifluoromethyl-phenylamino)-benzylcarbamoyl]-tetrahydrofuran-3-yl}-amide

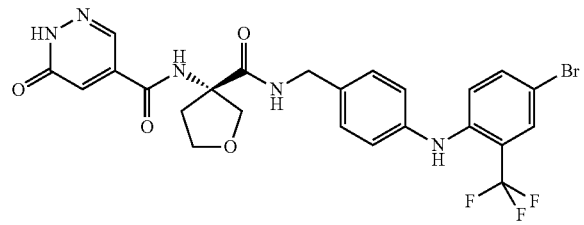 [SMILES: O=C(N[C@@]1(C(=O)NCc2ccc(Nc3ccc(Br)cc3C(F)(F)F)cc2)CCOC1)c1cn[nH]c(=O)c1]

Prepared from intermediates A9 and B1 according to AAV1.
$C_{24}H_{21}BrF_3N_5O_4$ (580.35)
$R_t$=2.32 minutes (method 2)

EXAMPLE 9

(S)-6-oxo-1,6-dihydro-pyridazine-4-carboxylic acid {3-[2-fluoro-4-(2-trifluoromethyl-phenylamino)-benzylcarbamoyl]-tetrahydro-furan-3-yl}-amide

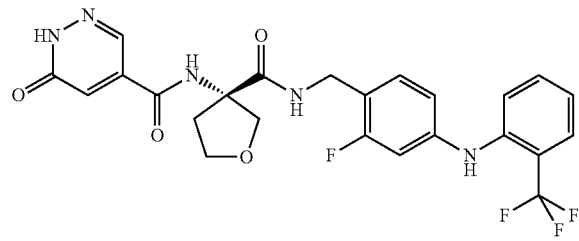 [SMILES: O=C(N[C@@]1(C(=O)NCc2ccc(Nc3ccccc3C(F)(F)F)cc2F)CCOC1)c1cn[nH]c(=O)c1]

Prepared from intermediates A5 and B1 according to AAV1.
$C_{24}H_{21}F_4N_5O_4$ (519.45)
$R_t$=1.35 minutes (method 7)
mass spectroscopy (ESI): [M+H]+=520
[M−H]−=518

The following Examples describe pharmaceutical formulations which contain as active substance any desired compound of general formula I, without restricting the scope of the present invention thereto:

EXAMPLE I

Dry Ampoule with 75 Mg of Active Compound Per 10 Ml
Composition:

| | |
|---|---|
| Active compound | 75.0 mg |
| Mannitol | 500 mg |
| Water for injection | ad 10.0 ml |

Production:

Active compound and mannitol are dissolved in water. The charged ampoules are freeze dried. Water for injection is used to dissolve to give the solution ready for use.

EXAMPLE II

Tablet with 50 Mg of Active Compound
Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

EXAMPLE III

Tablet with 350 Mg of Active Compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

EXAMPLE IV

Capsule with 50 Mg of Active Compound
Composition:

| | |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
| | 160.0 mg |

Production:
(1) is triturated with (3). This trituration is added to the mixture of (2) and (4) with vigorous mixing.
This powder mixture is packed into hard gelatine two-piece capsules of size 3 in a capsule-filling machine.

EXAMPLE V

Capsules with 350 Mg of Active Compound
Composition:

| | |
|---|---|
| (1) Active compound | 350.0 mg |
| (2) Maize starch dried | 46.0 mg |
| (3) Lactose powdered | 30.0 mg |
| (4) Magnesium stearate | 4.0 mg |
| | 430.0 mg |

Production:
(1) is triturated with (3). This trituration is added to the mixture of (2) and (4) with vigorous stirring.
This powder mixture is packed into hard gelatine two-piece capsules of size 0 in a capsule-filling machine.

EXAMPLE VI

Suppositories with 100 Mg of Active Compound
1 suppository comprises:

| | |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:

1. A compound of the formula I

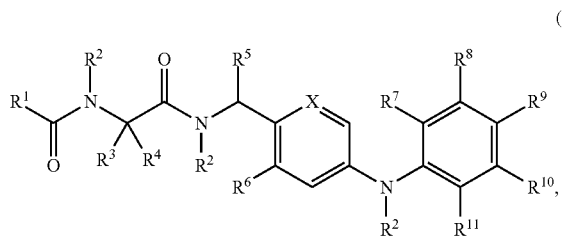

(I)

wherein
R$^1$ denotes the group

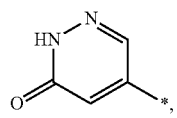

R$^2$ denotes H or CH$_3$,
R$^3$ and R$^4$ together with the carbon atom to which they are bound denote a C$_{3-6}$-cycloalkylene group wherein a —CH$_2$ unit may be replaced by an oxygen atom,
R$^5$ denotes H or CH$_3$,
R$^6$ denotes H, F, Cl or methyl,
R$^7$ denotes H, F, Cl, Br, —CN, C$_{1-4}$-alkyl, CF$_3$, CHF$_2$,
R$^8$ denotes H,
R$^9$ denotes F, Cl, Br, C$_{1-4}$-alkyl, —O—C$_{1-4}$-alkyl, —S—C$_{1-4}$-alkyl,
R$^{10}$ denotes H,
R$^{11}$ denotes F, Cl, Br, —CN, C$_{1-4}$-alkyl, CF$_3$, CHF$_2$, and
X denotes CH or N,
or a salt thereof.

2. A compound of the formula I according to claim 1, wherein R$^1$, R$^3$, R$^4$, R$^5$, R$^6$, R$^7$, R$^8$, R$^9$, R$^{10}$, R$^{11}$, n and X are defined as in claim 1 and
R$^2$ denotes H,
or a salt thereof.

3. A compound of the formula I according to claim 1 selected from the group consisting of:

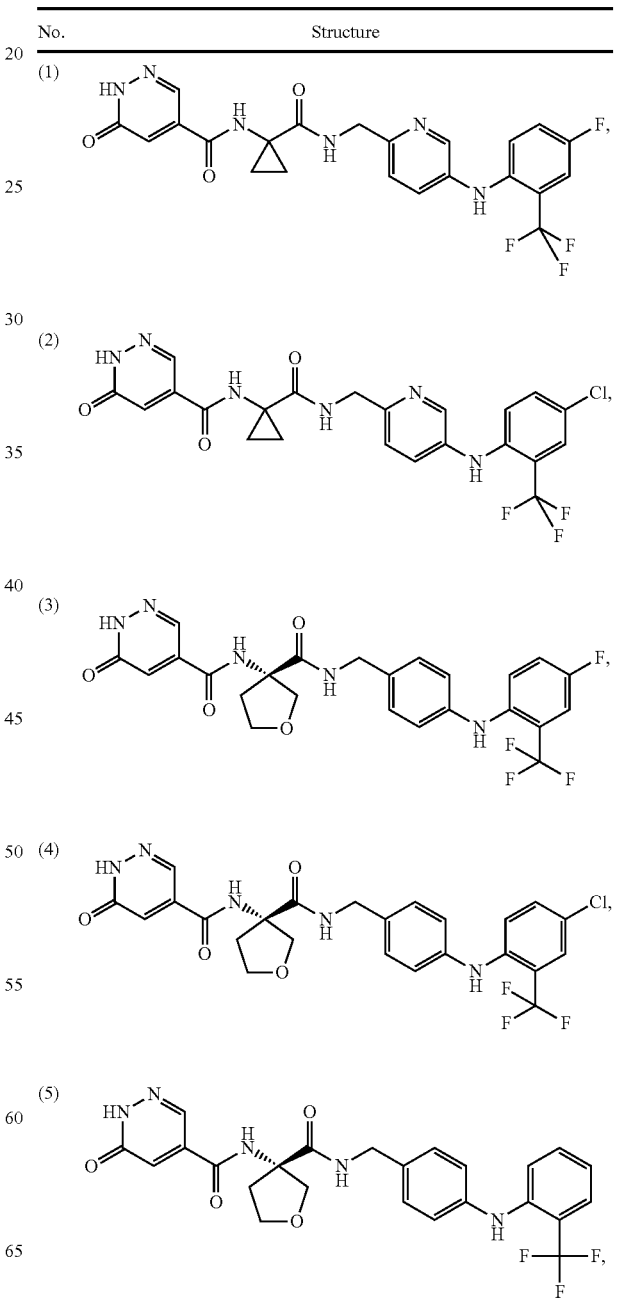

-continued

| No. | Structure |
|---|---|
| (6) | 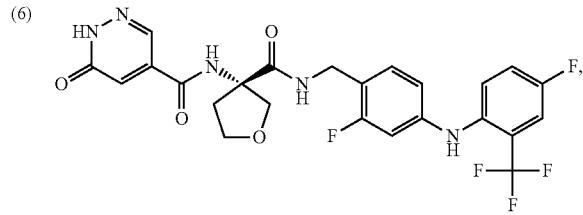 |
| (7) | 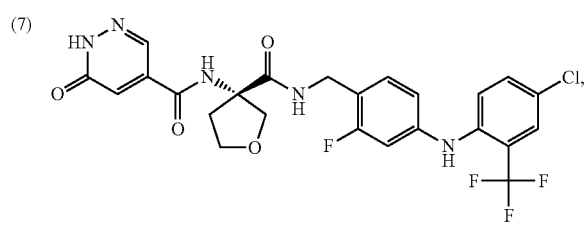 |
| (8) | 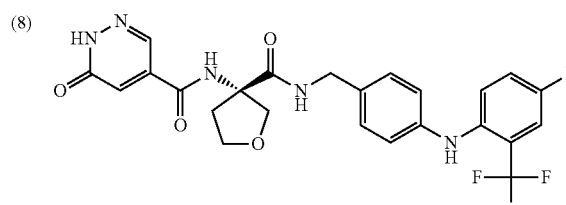 |
| | and |
| (9) | 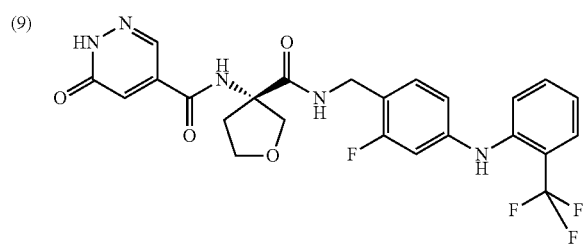 | or a salt thereof.

4. The compound according to claim 1 of the formula:

| No. | Structure |
|---|---|
| (1) | 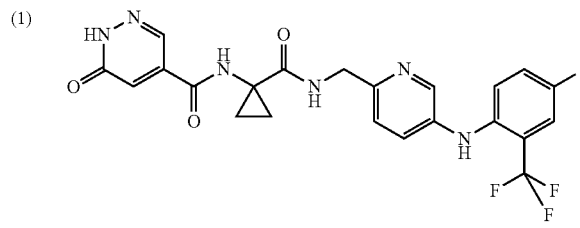 | or a salt thereof.

5. The compound according to claim 1 of the formula:

| No. | Structure |
|---|---|
| (2) | 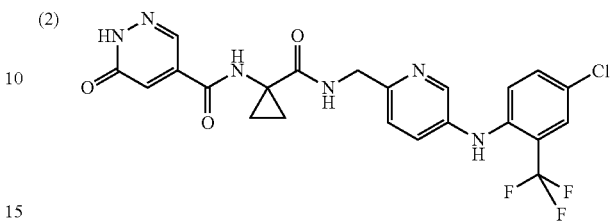 | or a salt thereof.

6. The compound according to claim 1 of the formula:

| No. | Structure |
|---|---|
| (3) | 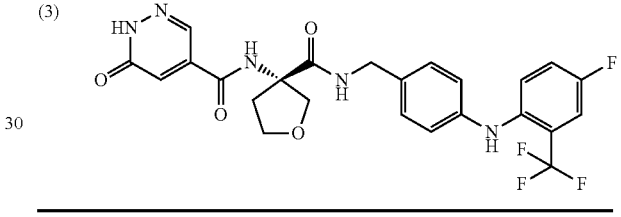 | or a salt thereof.

7. The compound according to claim 1 of the formula:

| No. | Structure |
|---|---|
| (4) | 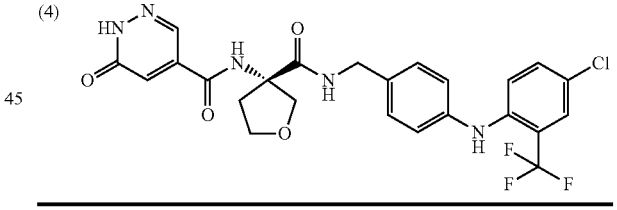 | or a salt thereof.

8. The compound according to claim 1 of the formula:

| No. | Structure |
|---|---|
| (5) | 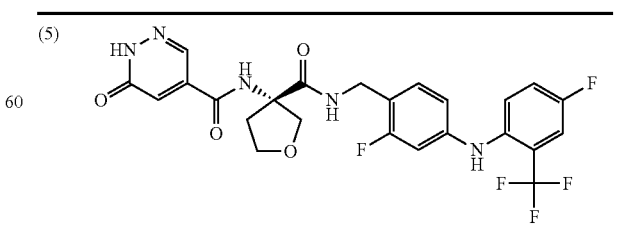 | or a salt thereof.

9. The compound according to claim 1 of the formula:

| No. | Structure |
|---|---|
| (6) | [structure: 6-oxo-1,6-dihydropyridazine-4-carboxamide linked to tetrahydrofuran-3-yl carboxamide-CH2-(2-fluoro-4-((4-fluoro-2-(trifluoromethyl)phenyl)amino)phenyl)] | or a salt thereof.

10. The compound according to claim 1 of the formula:

| No. | Structure |
|---|---|
| (7) | [structure: 6-oxo-1,6-dihydropyridazine-4-carboxamide linked to tetrahydrofuran-3-yl carboxamide-CH2-(2-fluoro-4-((4-chloro-2-(trifluoromethyl)phenyl)amino)phenyl)] | or a salt thereof.

11. The compound according to claim 1 of the formula:

| No. | Structure |
|---|---|
| (8) | [structure: 6-oxo-1,6-dihydropyridazine-4-carboxamide linked to tetrahydrofuran-3-yl carboxamide-CH2-(4-((4-bromo-2-(trifluoromethyl)phenyl)amino)phenyl)] | or a salt thereof.

12. The compound according to claim 1 of the formula:

| No. | Structure |
|---|---|
| (9) | [structure: 6-oxo-1,6-dihydropyridazine-4-carboxamide linked to tetrahydrofuran-3-yl carboxamide-CH2-(2-fluoro-4-((2-(trifluoromethyl)phenyl)amino)phenyl)] | or a salt thereof.

13. A physiologically acceptable salt of a compound according to claim 1, 2, 3, 4, 5, 6, 7, 8, 9, 10, 11 or 12.

14. A pharmaceutical composition comprising a compound according to claim 1, 2, 3, 4, 5, 6, 7, 8, 9, 10, 11 or 12 or a physiologically acceptable salt thereof together with one or more inert carriers and/or diluents.

15. A method for treating pain, visceral pain, neuropathic pain, inflammatory/pain receptor-mediated pain, tumour pain and headache diseases which comprises administering to a host suffering from such condition a therapeutically effective amount of a compound according to claim 1, 2, 3, 4, 5, 6, 7, 8, 9, 10, 11, 12 or a physiologically acceptable salt thereof.

* * * * *